United States Patent [19]
Wood et al.

[11] Patent Number: 5,472,871
[45] Date of Patent: Dec. 5, 1995

[54] ISOLATION AND CHARACTERIZATION OF THE NEMATODE HER-1 GENE AND PROTEIN PRODUCT

[75] Inventors: William B. Wood; Marc D. Perry, both of Boulder, Colo.; Carol Trent, Bellingham, Wash.

[73] Assignee: The University of Colorado Foundation, Inc., Boulder, Colo.

[21] Appl. No.: 194,180

[22] Filed: Feb. 9, 1994

Related U.S. Application Data

[63] Continuation of Ser. No. 844,294, Feb. 28, 1992, abandoned.
[51] Int. Cl.$^6$ .............................. C12N 1/21; C12N 15/03; C12N 15/12
[52] U.S. Cl. ........................ 435/252.3; 435/320.1; 435/252.34; 435/252.33; 435/172.3; 435/69.1; 536/23.5; 536/23.1; 536/23.51; 935/9; 935/11; 935/29; 935/30; 935/27; 935/28; 935/67; 935/68; 935/70; 935/72; 514/2; 514/12; 514/44
[58] Field of Search ................. 536/23.1, 23.5, 536/23.51; 435/240.2, 252.3, 252.33, 320.1, 172.3, 69.1, 69.2, 69.4; 514/2, 12, 44; 935/9, 11, 13, 19, 22, 23, 29, 32, 56, 60, 66, 70, 72, 73

[56] References Cited

U.S. PATENT DOCUMENTS 4,338,397  7/1982  Gilbert et al. ..................... 435/69.1

OTHER PUBLICATIONS

Lewin, R. 1987. Science 237, 1570.

Eide et al. 1985. Proc Nat'l. Acad. Sci. USA 82, 1756–1760.

Trent et al. 1988, Genetics 120, 145–157.

Coulson et al. 1986. Proc. Nat'l. Acad. Sci. USA. 83, 7821–7825.

Bagdasanian et al, 1979 "New vector plasmids for gene cloning in Pseudomonas, " in: Plasmids of Medical, Environmental and Commerical Importance (Timmis et al,; eds.), Elsevier/North—Holland Biomedical Press. pp. 411–422.

Brock T. D. 1979, in: Biology of Microorganisms, 3rd. editions Prentice—Hall, Inc. pp. 477–478.

Fire et al. 1990. Gene. 93, 189–198.

Studier et al. 1990. Meth. Enzymol. 185, 60–89.

Yansura et al. 1990. Meth. Enzymol 185, 54–60.

Gray et al. 1984 Bio/Technol. 2, 161–165.

Primary Examiner—Christopher S. F. Low

[57] ABSTRACT

The her-1 gene of *Caenorhabditis elegans* has been isolated and sequenced. The her-1 gene encodes an amino acid sequence which induces male differentiation. Methods for recombinantly producing the her-1 protein and for transforming plants, bacteria and fungi with the her-1 gene to express the her-1 protein are disclosed.

5 Claims, 8 Drawing Sheets

```
1441  gtaccttcttgtctaacttctctttgagtatctaagtctcttcaggttctatatccatcattcaaccaaatgacactgcagggATGCCTA
1531  TCTCCCTGACTGAACCCACCAGTCGTCTCTTGCTCATATTCCTCCTACCTTCTGCTTCTTCTCAGCGCATCTTGTCCACCTACAGTA
1621  GTAAATCTCCTCCCTTCCTTACGTTGCATTATGAGATATCTCCCAATTTTGTGTTTCTCGGATCATTTGGCTATACGGAAACTACATT
            M  R  Y  L  P  I  F  V  F  L  G  S  F  G  Y  T  E  T  T  L
1711  AACAAAGGAACTTATCAAAGATGCAGCTGAGAAATGCTGTACAAGAATCCGTCAAGAATGTTGCATTGAAATTATGAAATTTGGgtgaac
  21   T  K  E  L  I  K  D  A  A  E  K  C  C  T  R  N  Q  E  C  C  I  E  I  M  K  F  G
1801  cgcttttacgagcacgaacaatgcgataatcggtataattagAACCCCAATTCGATGTGGTTATGACAGGATCCGAAGCTACCCGGAT
                                               T  P  I  R  C  G  Y  D  R  D  P  K  L  P  G  Y
1891  ATGTCTACAAATGTCTTCAAAAATGTGTTGTTTGCAAAAGAACCAAAGAAAAAGATTAACTTGGATGgt//      //aagagactttccca
  65   V  Y  K  C  L  Q  N  V  L  F  A  K  E  P  K  K  K  I  N  L  D  D     Intron 2
5131  aaagaaatcgttatttttgagggacaaattgtcttaattatcgatctattattgcctcttcacacgtaaacatgccaacacctgtctc
                                                                                       SL1
5221  tttgactccgcctctctgattgcccgcccattgcccatcccacgcccaatctcatattgtctttattcagACTCCGTGTGCTGCTC
                                                                              S  V  C  C  S
```

FIG. 2

```
5311 CGTGTTTGGCAACGACCAAAACGATTCTGGAAGAAGATGTGAGAATCGTTGCAAGAACCTCATGACCAGCCCTTCCATCGACGCTGCCAC
 92   V  F  G  N  D  Q  N  D  S  G  R  R  C  E  N  R  C  K  N  L  M  T  S  P  S  I  D  A  A  T
                          *  *        +        +                          +

5401 ACGTCTGGACAGCATCAAAAGTTGCTCGCTTCTGGATAATGTACTGTATAAAgtgagttttgttaacacagaatt//
122   R  L  D  S  I  K  S  C  S  L  L  D  N  V  L  Y  K                              Intron 3

5941 //acaaattatttcagTGTTTTGAGAAATGCCGGAGCCTCCGTAAAGATGGTATCAAAATTGAAGTGCTCCAATTCGAAGAATAC
                    C  F  E  K  C  R  S  L  R  K  D  G  I  K  I  E  V  L  Q  F  E  E  Y
                                     +        +  .

6031 TGCAATGCAAACGTTTATCCAAAGCGAACTTTCCGAGGAGTCTGAATCTGGGCTCATTAGCCTAAAACATCCCTAATCCGCCGTTGTCAT
162   C  N  A  T  F  I  Q  K  R  T  F  F  R  G  V  *
      *  *                 +

6121 TATGGCACTCTCCATCATGAGTGTCCAATTTTTTCTTCTTTCTAAACCTTTTTATTTTCTAAACACCTCTATGTCTACCTC
6211 TTAATCAAAGCTTTGAGCTTTACTCACTTTGAGTTATATCTTGTGTTCTCCTTATGTTGAAGAAAATTTTCGATACGCAACTT
6301 GTCATATTGTTGTATATATTTTAATAGAATTTTTGAAATGTCCTATTCTTATTGATTCTCTTAACATTCTCCTTCAAGAATGTTTTC
6391 GGATGCGCTCAGATGTCATGAAGGCGCACTACGGTGCGTCCTGATTTTATTTATTTATTTTTCATAAAAAATATATCTTCTCTTGTTGG
6481 TTTCTCCTAAAGTTGTCAAATAGAATATTCAAGTACTTTCTACGATCTTTTTATTGAATAAAAttgttttatcaacgcacagaacccata
```

FIG. 2 (CON'T)

```
==============                                                    30                                    60
MRYLPIFVFLGSFGYTETTLTKELIKDAAEKCCTRNRQECCIEIMKFGTPIRCGYDRDPK
==============                                                                *
                                                                  90                                   120
LPGYVYKCLQNVLFAKEPKKKINLDDSVCCSVFGNDQNDSGRRCENRCKNLMTSPSIDAA

150
TRLDSIKSCSLLDNVLYKCFEKCRSLRKDGIKIEVLQFEEYCNATFIQKRTFRGV
```

FIG. 3

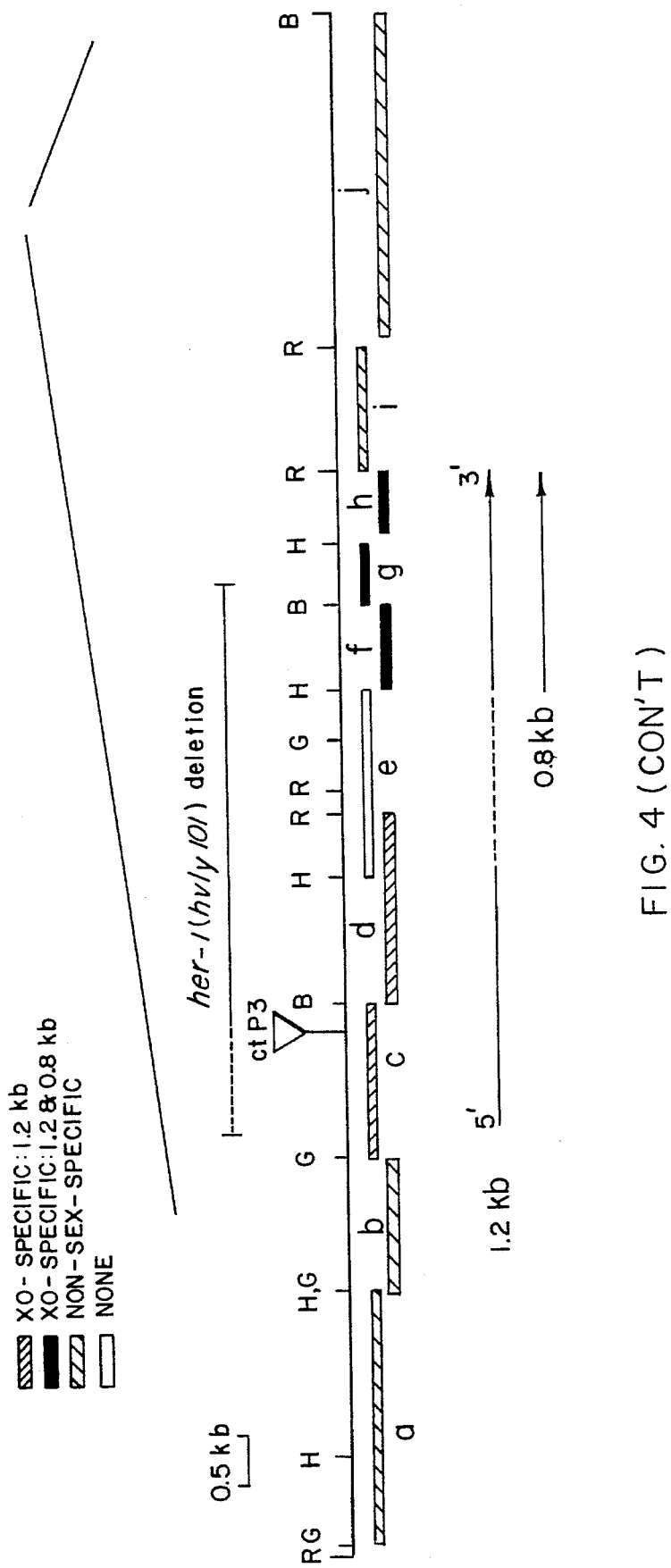
FIG. 4 (CON'T)

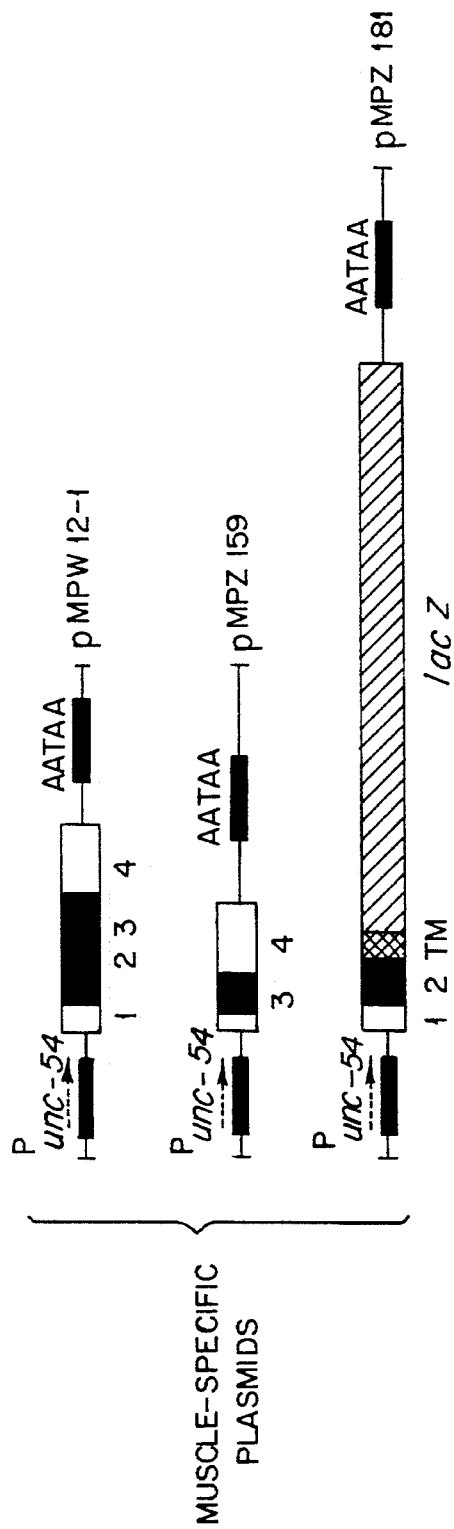
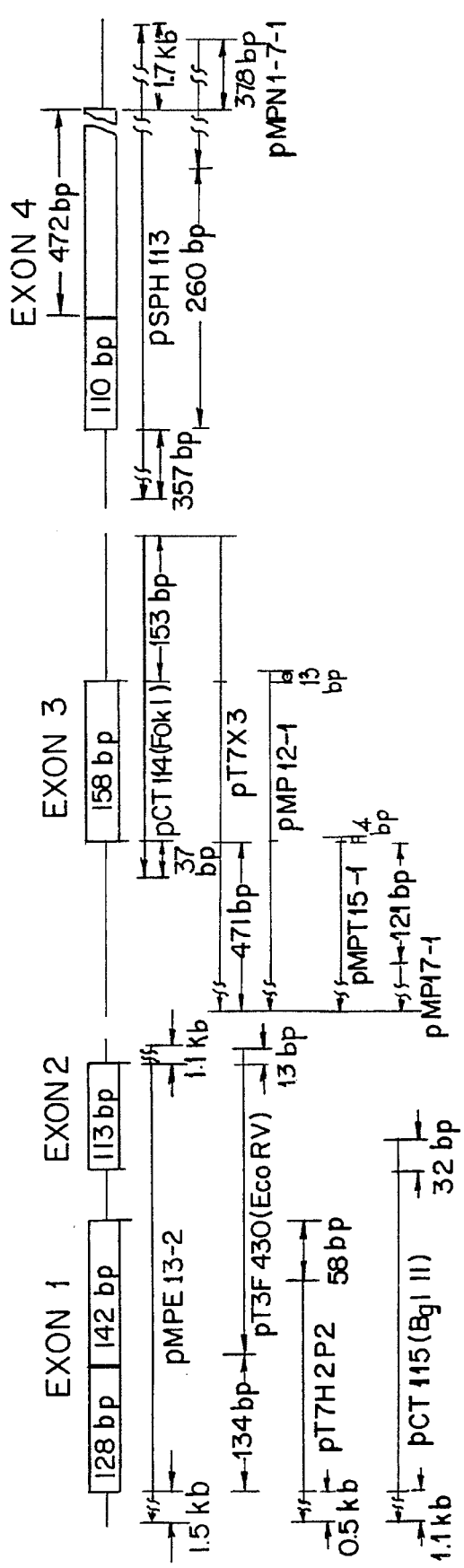
FIG. 5B
FIG. 5C

ISOLATION AND CHARACTERIZATION OF THE NEMATODE HER-1 GENE AND PROTEIN PRODUCT

This invention was made in part with funding from the National Institutes of Health (grants no. HD-11762 and GM-43333). The United States Government may have certain rights in this invention. This is a continuation of application Ser. No. 07/844,294 filed on Feb. 28, 1992, now abandoned.

FIELD OF THE INVENTION

This invention relates to the isolation and sequencing of the her-1 gene of *Caenorhabditis elegans*, a developmental control gene which induces male differentiation, and to the discovery that one product of the her-1 gene is a small secreted protein. The sequence of the her-1 gene and the predicted sequence of the her-1 protein are disclosed.

This invention further discloses methods of using the her-1 gene and protein product to control nematode infestation of plants, animals, and humans by inducing parasites to develop exclusively as males. This includes subcloning the her-1 nucleic acid sequence into an expression vector, and use of the vector to express biologically active her-1 protein suitable for use in pharmaceutical or pesticidal compositions. Further described are methods for transformation of plants, bacteria, and fungi with the her-1 gene to express the her-1 protein.

BACKGROUND OF THE INVENTION

Members of the phylum Nematoda are numerous and diverse, having adapted to existence in most terrestrial and marine environments. Despite their diverse habitats and life-styles, all nematodes are morphologically and developmentally similar. Some nematode species are free-living; others parasitize a wide variety of plant and animal hosts.

Damage to commercially important crops such as corn and soybeans in the U.S. alone due to plant parasitic nematodes is estimated to be about $5 billion annually. Parasitic nematode species, such as Meloidogyne, feed off plant root tissues and lay eggs that hatch into larvae, which then infest other plants. Nematodes of several species, many of which reproduce parthenogenetically, infect plant roots as sexually uncommitted larvae. Their sexual development is influenced by unknown environmental signals that depend on the health of the plant and the population density of infecting nematodes. If conditions are favorable, the larvae develop into females, which continue to feed, grow, and lay eggs with debilitating effects on the plant; if conditions are unfavorable, the larvae develop into males, which leave the root without causing significant harm. Therefore, damage by the parasite, as well as further reproduction, may be prevented by an agent that induces male development.

Debilitating diseases in domestic animals as well as humans are caused by a variety of nematode parasites that infect and reproduce in the gut, bloodstream, or other tissues. Parasitic nematodes are estimated to affect over a billion people worldwide, primarily in third world countries. These nematodes are almost all sexually reproducing species that require both males and females to be present in the host for reproduction. Therefore, an agent that induces all parasites to develop as males would prevent further reproduction.

*Caenorhabditis elegans* (*C. elegans*) is a small, free-living soil nematode found commonly in many parts of the world. It feeds primarily on bacteria and reproduces with a life cycle of about 3 days under optimal conditions. The early embryonic cell divisions include a series of asymmetric asynchronous cleavages in which the germ line acts as a stem-cell lineage, giving rise sequentially to the founder cells (generally five) for the somatic tissue lineages, and finally to the germ line founder cell. Postembryonically, nematodes develop through four larval stages (L1–L4) characterized by different cuticle structures. Among parasitic species, the different larval stages often have evolved to become highly specialized for survival in a particular host or host tissue. Developmentally, some parasite nematodes remain sexually uncommitted until the L4 larval stage.

*C. elegans* exists as two sexes, a self-fertilizing hermaphrodite and a male. Hermaphrodites have two X (XX) chromosomes, produce both oocytes and sperm, and can reproduce either by self-fertilization or by cross-fertilization with males (XO). A hermaphrodite that has not mated lays about 300 eggs during its reproductive life span. Self-progeny broods consist almost entirely of XX hermaphrodites. Cross-fertilization broods are composed of equal numbers of XX hermaphrodites and XO male cross-progeny. Additionally, XO males arise spontaneously at a low frequency (0.2%) in self-fertilizing hermaphrodite populations as a result of meiotic X-chromosome nondisjunction (Hodgkin et al. (1979) Genetics 91:67–94). Many nematode species related to *C. elegans* have only true females and males and must reproduce by cross-fertilization. The *C. elegans* hermaphrodite can be viewed as a modified female that has acquired the ability to produce a small number of sperm in the germ line before switching to oogenesis (Villeneuve and Meyer (1990a) Adv. Genet. 27:117–188).

*C. elegans* is a relatively simple organism anatomically and genetically. The adult hermaphrodite contains only 959 somatic nuclei, and the adult male only 1031 (Wood (1988) in The Nematode *Caenorhabditis elegans*, W. B. Wood, ed. (Cold Spring Harbor Laboratory: Cold Spring Harbor, N.Y.), pp. 1–16). The degree of sexual dimorphism, however, is extensive and affects the fates of over 30% of the adult somatic cells. The primary sex determination signal in *C. elegans* is the ratio of the number of X chromosomes to the number of sets of autosomes: the X:A ratio (Nigon (1951) Biol. Bull. Fr. et Belg. 95:187–225; Madl and Herman (1979) Genetics 93:393–402). Diploid animals with two XX chromosomes (2X/2A=1), triploid animals with three X chromosomes (3X/4A=0.75), and tetraploid animals with four X chromosomes (4X/4A=1), are hermaphrodite. Diploid animals with a single X chromosome (1X/2A=0.5) or tetraploid animals with two X chromosomes (2X/4A=0.5) are male, and triploid animals with two X chromosomes (2X/3A=0.67) are usually male. Thus, a ratio of 0.75 or greater elicits hermaphrodite development, while a ratio of 0.67 or less results in male development.

Ten genes have been identified that are required to assess and transmit the primary signal to the genes responsible for generating sexual dimorphism (for reviews, see Hodgkin (1988) in The Nematode *Caenorhabditis elegans*, W. B. Wood, ed. (Cold Spring Harbor Laboratory: Cold Spring Harbor, N.Y.), pp. 243–280, and Meyer (1988) Trends Genet. 4:337–342). The ten genes are divided into two classes: (1) X-linked genes that have roles in dosage compensation as well as sex-determination, including three sdc (sex determination and dosage compensation) genes, and the xol-1 (XO lethal) gene, and (2) autosomal genes that are involved only in sex determination, including three tra (transformer) genes, the her-1 (hermaphroditization) gene, and three fem (feminization) genes.

Regulatory genes exhibiting two classes of mutations that result in opposite (or reciprocal) phenotypes have been dubbed "switch" genes because the levels of their products are correlated with one of two alternative developmental decisions (Hodgkin (1984) J. Embryology Exp. Morph. 83: 103–117 (supplement); Sternberg and Horvitz (1984) Ann. Rev. Genet. 18:489–524). Several genes in the *C. elegans* sex determination pathway are switch genes: tra-1 (Hodgkin (1987) Ann. Rev. Genet. 21:133–154, and (1988) Genes and Develop. 1:731–745), tra-2 (Doniach (1986) Genetics 114:53–76), fem-3 (Barton et al. (1987) Genetics 115:107–119), and her-1 (Hodgkin (1980) Genetics 96:147–164).

The her-1 gene functions at the first step of the sex determination process and is required for male but not for hermaphrodite development (Hodgkin (1980) supra). The gene is defined by over twenty-five recessive loss-of-function (lf) mutations, most of which completely transform XO males into XO self-fertile, anatomically normal hermaphrodites (Hodgkin (1980) supra; Trent et al. (1988) Genetics 120:145–157). Two dominant gain-of-function (gf) her-1 mutations that map to the same locus (n695 and y101) result in the opposite phenotype: XX animals are variably masculinized into pseudo-males; XO animals are unaffected (Trent et al. (1983) Genetics 104:619–647, and (1988) supra). Thus, active her-1 gene product is required for normal male development in XO animals, and its presence is sufficient to induce male differentiation and prevent female development in XX animals.

Hodgkin (1980) supra, has proposed a model in which the her-1, tra, and fem genes regulate sex determination via a hierarchical pathway involving several negative regulatory interactions, shown in FIG. 1. According to this model the X:A ratio sets the activity state (high or low) of the her-1 gene, and the her-1 gene in turn, via the tra-2, tra-3, and fem genes, sets the state of the tra-1 gene, which controls subsequent sexual differentiation. More specifically, her-1 acts as a negative regulator of tra-2 and tra-3, which in turn negatively regulate the fem genes. The fem genes act as negative regulators of tra-1.

This model suggests that in wild-type *C. elegans* sex determination a variable quantitative primary signal, the X:A ratio, is integrated and transduced into a secondary binary developmental signal: her-1 activity is high (if the X:A ratio is low as in XO animals) or her-1 activity is low (if the X:A ratio is high as in XX animals). How the X:A ratio is assessed and how this signal is relayed to her-1 is not known, although the xol-1, sdc-1, and sdc-2 genes are known to have important roles in this process, and the two sdc genes are known to function as negative regulators of her-1 (Miller et al. (1988) Cell 55:167–183; Villeneuve and Meyer (1987) Cell 48:25–37 and (1990a) supra; Nusbaum and Meyer (1989) Genetics 122:579–593). The regulatory pathway of sex determination in *C. elegans* (FIG. 1) appears to operate in two different states in the two sexes. In XX hermaphrodites, where the X:A ratio is high, xol-1 activity is low; therefore, sdc-1 and scd-2 activities are high, and her-1 activity is low. In XO males, where X:A is low, xol-1 activity is high; therefore, sdc-1 and sdc-2 activities are low, and her-1 activity is high. The terminal regulator, tra-1, whose activity is high in XX animals and low in XO animals, controls a variety of downstream sexual differentiation genes (Villeneuve and Meyer (1990a) supra).

This application describes the isolation, sequencing, and expression of the her-1 nucleic acid sequence encoding a protein product that prevents female development and activates the male developmental pathway in nematodes. Further, the her-1 protein has been discovered to be a secretory protein capable of exerting its masculinizing effect on cells exposed to it. This suggests that the her-1 nucleic acid sequence and protein may be useful for the control of parasitic nematodes in plants, animals, and humans.

Although the her-1 gene described herein was isolated from *C. elegans*, the protein product of the her-1 gene is expected to activate male development in other members of the phylum Nematoda since fundamental sex determining mechanisms are expected to be conserved among different classes of nematodes. Further, the present invention encompasses use of the methods herein described for isolation of the equivalent gene in other species of nematodes, as well as the isolation or synthesis of other molecules which mimic the biological activity of her-1.

BRIEF SUMMARY OF THE INVENTION

This invention relates to and claims the purified and isolated nucleic acid sequence shown in FIG. 2 (SEQ ID NO:1 and SEQ ID NO:2) encoding for the amino acid sequence shown in FIG. 3 (SEQ ID NO:3). This invention encompasses a nucleic acid sequence with substantial homology to the nucleic acid sequence shown in FIG. 2 (SEQ ID NO:1 and SEQ ID NO:2), or a subsequence thereof. The present invention encompasses use of the her-1 gene sequence for isolation of the equivalent gene in other animals. This invention further includes a nucleic acid sequence capable of hybridizing to the complementary sequence of the nucleic acid sequences of FIG. 2 (SEQ ID NO:1 and SEQ ID NO:2). Further included in this invention is a nucleic acid sequence encoding an amino acid sequence capable of inducing male differentiation in nematodes, such amino acid sequence being recognized by an antibody which binds portions of the her-1 protein.

This invention includes an expression vector comprising expression regulatory sequences operatively linked to a nucleic acid sequence selected from the group consisting of: (a) a nucleic acid sequence which encodes an amino acid sequence as set forth in FIG. 3 (SEQ ID NO:3), (b) a nucleic acid sequence which encodes an amino acid sequence which induces male differentiation in nematodes, (c) a nucleic acid sequence which encodes an amino acid sequence recognized by an antibody which binds a portion of the her-1 protein, and (d) a nucleic acid sequence which is a subsequence of any one of the nucleic acid sequences of (a), (b), or (c) which encode forms of the her-1 protein which differ in molecular weight from each other and which forms of her-1 induce male differentiation in nematodes and are recognized by an antibody which binds to portions of the her-1 protein.

This invention describes and includes the sex-specific RNA transcript products of the her-1 gene. A 1.2 kb transcript is predicted to encode a 175-amino acid protein. A 0.8 kb transcript is predicted to encode a 64-amino acid protein corresponding to the C-terminal 64 amino acids of the 175-amino acid protein.

This invention describes and includes the inferred amino acid sequence of two her-1 proteins (FIG. 3), a 175-amino acid protein (SEQ ID NO:3) and the C-terminal 64 amino acids of the same protein (SEQ ID NO:4 (in brackets)). This invention includes amino acid sequences having substantial homology to the amino acid sequence of FIG. 3 (SEQ ID NO:3) or portions thereof. This invention further includes an amino acid sequence which induces male differentiation in nematodes. Further included in this invention is an amino acid sequence recognized by an antibody which binds to portions of the her-1 protein. This invention contemplates that the her-1 protein may be biologically active as a monomer or a dimer, or as part of a larger molecule.

This invention includes a host cell transformed with an expression vector containing expression regulatory elements operatively linked to a nucleic acid sequence selected from the group consisting of: (a) a nucleic acid sequence which encodes the amino acid sequence set forth in FIG. 3 (SEQ ID NO:3), (b) a nucleic acid sequence which encodes an amino acid sequence which induces male differentiation in nematodes, (c) a nucleic acid sequence which encodes an amino acid sequence recognized by an antibody which binds a portion of the her-1 protein, and (d) a nucleic acid sequence which is a subsequence of any one of the nucleic acid sequences of (a), (b), or (c) which encode for forms of the her-1 protein which differ in molecular weight from each other and which forms of her-1 induce male differentiation in nematodes and are recognized by an antibody which binds to portions of the her-1 protein.

This invention includes a recombinant DNA method for the production of the her-1 protein comprising (a) subcloning a nucleic acid sequence encoding the her-1 protein into an expression vector which comprises the regulatory elements needed to express the DNA sequence; (b) transforming a host cell with said expression vector; (c) culturing the host cell under conditions for amplification of the vector and expression of the her-1 protein; and (d) harvesting the her-1 protein from the culture medium. The recombinant DNA method of this invention contemplates use of the nucleic acid sequence set forth in FIG. 2 (SEQ ID NO:1 and SEQ ID NO:2).

This invention includes a method of using the her-1 protein for the control of nematode infestation of plants, animals, and humans. This method encompasses direct application of her-1 protein, or a derivative or mimetic thereof, to plants and soil to induce sexually-uncommitted nematode embryo and larvae to develop into male animals.

This invention also includes use of the her-1 nucleic acid sequence in genetically engineered bacteria, including soil and rumen bacteria, such bacteria being capable of expressing the her-1 protein.

This invention further includes use of the her-1 nucleic acid sequence in genetically engineered plants, plant tissue, and plant cells, such that the resulting transgenic plants are capable of expressing the her-1 protein.

This invention also includes pharmaceutical compositions for the treatment of nematode infections in animals and humans comprising an effective amount of purified her-1 protein, or a derivative or mimetic thereof, in a pharmaceutically acceptable carrier.

This invention also includes pesticidal compositions for the control of nematodes in plants and soil comprising biologically active her-1 protein, or a derivative or mimetic thereof, in an agronomically acceptable carrier.

This invention further includes a method of controlling nematode infestation of plants comprising genetically engineering endophytes to express the her-1 protein and inoculating plants with the such endophytes.

It is to be understood that both the foregoing general description and the following detailed description are exemplary and explanatory only, and are not restrictive of the invention as claimed. The accompanying drawings, which are incorporated in and constitute a part of the specification, illustrate various embodiments of the invention and, together with the description, serve to explain the principles of the invention.

BRIEF DESCRIPTION OF THE DRAWINGS

FIG. 2 and FIG. 2 (cont') shows the genomic DNA and cDNA sequences (SEQ ID NO:1 and SEQ ID NO:2) of the her-1 gene. The predicted translation product is shown below, numbered from the first methionine codon. The secretion signal is underlined with "===", and two sites for potential N-linked glycosylation are marked as "***". Paired dibasic amino acid residues are marked with "+" and a repeated heptad in each promoter is marked ">>>>>>>".

FIG. 3 shows the predicted amino acid sequences of the 175-amino acid (SEQ ID NO:3) and the 64-amino acid SEQ ID NO: 4 (in brackets), her-1 proteins. The secretion signal is underlined with "===".

FIG. 4B shows the physical map and transcribed areas of the cloned region that includes the her-1 gene. The location of the ctP3 Tc1 insertion and the extent of the deletion in the her-1(hv1y101) mutation are shown. The restriction fragments designated a through j are shown as are the sex-specific transcripts detected.

FIGS. 5A, 5B, and 5C show the physical map of the her-1 locus and constructs for ectopic expression experiments. FIG. 5A shows a genomic restriction map. Boxes below the restriction map show the locations of the four her-1 exons contained in the mRNAs and cDNAs; white boxes indicate untranslated regions of the mRNA and black boxes indicate coding stretches. "ATG" marks presumed points of translation initiation. "P1" and "P2" denote the approximate locations of the two XO-specific her-1 promoters, the arrows indicate the direction of transcription. Abbreviations for restriction enzyme recognition sites are: H3 for HindIII; Sac for SacI; Pst for PstI; Bam for BamHI; RI for EcoRI. Individual exons of the her-1 gene are numbered: 1, 2, 3, 4; introns (not numbered) are counted from left to right starting with intron 1 between exon 1 and 2. FIG. 5B shows the plasmid constructs used in the ectopic expression experiments. pMPW12-1 contains the her-1 cDNA sequence corresponding to the 1.2 kb transcript; pMPZ159 contains the cDNA sequence corresponding to the 0.8 kb transcript; and pMPZ181 contains the her-1 cDNA sequence corresponding to exon 1 and a portion of exon 2 fused in frame to an artificial transmembrane domain (TM) followed by a lacZ coding sequence. FIG. 5C show the probes used in the RNAase protection mapping of her-1 exons experiments.

DETAILED DESCRIPTION OF PREFERRED EMBODIMENTS

Figure 1:
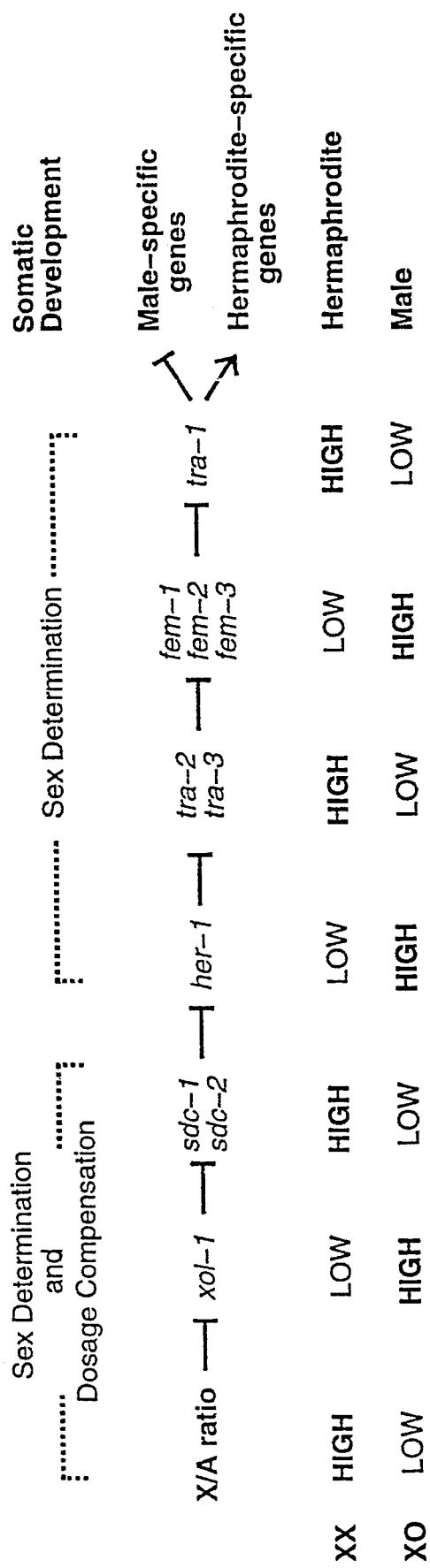
FIG. 1 shows the regulatory pathway governing somatic sexual phenotype in C. elegans. Barred arrows indicate that one gene negatively affects the function of another gene.

Reference will now be made in detail to the presently preferred embodiments of the invention which, together with the following examples, serve to explain the principles of the invention.

Prior to this invention, the her-1 gene had been genetically defined and assumed to be required for normal male development in C. elegans. The her-1 gene had not been isolated, and the secretory nature of the her-1 gene product was not known.

As described herein, a detailed description of the cloning of the her-1 gene and its nucleic acid sequence is provided, along with descriptions of the transcripts expressed from the her-1 gene and the inferred proteins translated from those transcripts. Also described is the utility of the her-1 protein; useful compositions containing it; vectors containing nucleic acid sequences coding for it; host cells transformed by such vectors; recombinant techniques for its production; and other aspects of the invention.

The cloning of the her-1 gene is described below. The present invention encompasses use of the her-1 gene sequence for isolation of the equivalent gene in other animals. Those skilled in the art will appreciate that other methods for cloning the her-1 gene are obvious in light of the description herein. In particular, the cloning of genes from other species encoding the her-1 gene or gene family will be obvious in view of the disclosures and procedures described herein.

This invention includes means for identifying and cloning genes that encode proteins that share amino acid sequence homology with the her-1 protein. The her-1 gene displays no significant homology to any previously described gene, but unidentified genes may exist that encode proteins that have substantial amino acid sequence homology to the her-1 protein and which could function with a similar biological activity in vivo as the her-1 protein. Such proteins would constitute members of the her-1 family. Under appropriate hybridization conditions, nucleic acid "cross-hybridization" could occur between genes within the family, i.e., a nucleic acid probe derived from the sequence of one of the family members will form a stable hybrid duplex molecule with nucleic acid molecules from different members of the family which have sequences related, but not identical, to the probe (Beltz et al. (1983) Methods Enzymol. 100:266–285). Therefore, one may screen for genes related by sequence homology to her-1 by preparing unique or degenerate DNA (or RNA) probes based on the sequence of the her-1 gene from different species and performing hybridization experiments with a variety of target DNAs (or RNAs) under conditions that will allow stable formation of imperfectly paired nucleic acid duplexes.

Such hybridization conditions, often termed "reduced stringency" are well described in the literature (Beltz et al. (1983) supra, Sambrook et al. (1989) *Molecular Cloning: A Laboratory Manual,* 2d ed. (Cold Spring Harbor Laboratory: Cold Spring Harbor, N.Y.) and most frequently involve reduction in temperature of the hybridization reaction when carried out in aqueous solution and/or reduction in concentration of formamide in hybridization systems normally employing solutions containing 50% formamide. Other means of reducing hybridization stringency have also been described and could be employed (Sambrook et al. (1989) supra). The nucleic acid targets in these hybridization experiments could include:

1) genomic DNA libraries of any nematode species cloned into any convenient vector including bacteriophages, plasmids, cosmids, yeast artificial chromosomes, or any other type of vector;

2) cDNA libraries generated from RNA from any tissue type obtained from any nematode species or obtained from culture of any type of primary cell obtained from any nematode species, or from any type of stable cell line currently existing or produced from any primary cell culture;

3) genomic DNAs as described in item 1 above which are digested with restriction enzymes and prepared for Southern blot analysis by gel electrophoresis and transferred onto a solid support;

4) RNAs as described in item 2 above which are subject to electrophoresis and transferred to a solid support for Northern blot analysis. Such RNAs could include total cellular RNA or fractionated poly $A^+$ RNA.

5) products of polymerase chain reactions (PCR) which employ oligonucleotide primers based on sequences occurring in her-1 and employing as templates any of the nucleic acid sources described in items 1 through 4.

Any nucleic acid sequence which is demonstrated to hybridize to a her-1-based probe under some empirically determined set of hybridization conditions may be cloned and sequenced by any of a variety of techniques well known to one skilled in the art and the degree of sequence homology may be directly determined to identify members of a her-1 gene family.

An alternative method for identifying her-1 family members involves use of PCR to amplify sequences from her-1 family members followed by cloning and analysis of amplified sequences. Degenerate (or nondegenerate) oligonucleotide primers for PCR may be synthesized based on the her-1 sequence. PCR reactions may be performed under conditions of reduced annealing temperatures which would allow amplification of not only the her-1 sequences but the sequences of any her-1 family members. See, Innis et al. (1990) PCR Protocols: A Guide to Methods and Applications (Academic Press, San Diego). The products of such PCR reactions may be size selected by gel electrophoresis, cloned into an appropriate vector, and the cloned DNA sequenced to identify her-1 family members. Alternatively, the clones may first be screened by hybridization to a probe specific for her-1 under conditions of high stringency to identify her-1 clones. Any clones that fail to hybridize to her-1 under high stringency would then be sequenced or such clones could be hybridized to a her-1 probe under conditions of reduced stringency and any clones that did hybridize to the her-1 probe under these conditions would be sequenced.

A second approach using PCR for cloning her-1 family members would be to label the products of the PCR reaction and use those products as a probe to screen nucleic targets enumerated above under conditions of high and/or low stringency. Hybridizing clones or nucleic segments could be analyzed to identify her-1 clones and family members.

The products of the her-1 gene are described below. It is to be understood that this aspect of the invention covers any protein having an amino acid sequence the same or substantially homologous to that given in FIG. 3.

Throughout this specification, any reference to her-1 proteins should be construed to refer to proteins of any origin which are substantially homologous to and which are biologically equivalent to the her-1 proteins as characterized and described herein.

The present invention encompasses glycosylated and nonglycosylated forms of the her-1 protein, as well as truncated forms of the naturally-occurring and recombinant her-1 protein as described herein. In one further embodiment, her-1 is modified by attachment of one or more polyethylene glycol (PEG) or other repeating polymeric moieties. The present invention also encompasses her-1 produced by recombinant DNA methods in bacterial expression systems containing an amino-terminal methionine residue.

The present invention includes the mature and precursor forms of proteins encoded by the her-1 gene, and their biological equivalent. Throughout this application, the mature form of the her-1 proteins refers to the biologically active form of the protein as it exists in nature after proteolytic cleavage. The precursor form of the her-1 proteins refers to the proteins encoded for by the her-1 gene prior to proteolytic cleavage.

By "biologically equivalent" as used throughout the specification and claims, we mean compositions of the present invention which are capable of promoting male development in nematodes. By "substantial homology" as used throughout the ensuing specification and claims, is meant a degree of homology or similarity to the native her-1 proteins in excess of that displayed by any previously reported protein. Preferably, the degree of homology is in excess of 70%, most preferably in excess of 80%, and even more preferably in excess of 90%, 95%, or 99%. A particularly preferred her-1 protein is in excess of 95% homologous with the native proteins. The percentage of homology as described herein is calculated as the percentage of amino acid residues found in the smaller of the two sequences which align with identical amino acid residues in the sequence being compared when four gaps in a length of 100 amino acids are introduced to assist in that alignment, as set forth by Dayhoff, in *Atlas of Protein Sequences and Structure* Vol. 5, p. 124 (1972), National Biochemical Research Foundation, Washington, D.C., specifically incorporated herein by reference. Also included as substantially homologous are those proteins which may be isolated by virtue of cross-reactivity with antibodies to the described proteins or whose genes may be isolated through hybridization with the gene or with segments of the described genes. Antibodies to the proteins described herein may be prepared according to standard procedures by those of ordinary skill in the art.

The her-1 protein dictates male development in *C. elegans*. It is contemplated that the her-1 gene and protein are useful in preventing female development and inducing male differentiation in all members of the *Nematoda phylum* and that the biological active molecule may be a monomer or dimer.

The present invention further encompasses natural and synthetic mimetics biologically equivalent to the her-1 protein in preventing female development and inducing male differentiation in nematodes. The disclosure of the sequence of the her-1 protein will enable those skilled in the art to predict and synthesize molecules mimicking the biological action of her-1.

1. Cloning of her-1 Gene

This invention describes the nucleic acid sequence of the her-1 gene coding for the protein which dictates male development in nematodes. General methods for culturing nematodes are described in Example 1. This invention includes a detailed method for cloning the her-1 gene sequence, as described in Example 2. Those skilled in the art will appreciate that other methods for cloning such a sequence are obvious in light of the disclosure herein. In particular, the cloning of genes from other members of the phylum Nematoda will be obvious in view of the disclosures and procedures described herein.

The her-1 gene was isolated by use of the transposon tagging technique, whereby insertion of the *C. elegans* transposable element Tc1 into the her-1 gene results in loss of her-1 function. A strain carrying a Tc1-induced recessive her-1 mutation was isolated and a Tc1-containing DNA fragment (ctP3) linked to her-1 identified by restriction fragment length polymorphism (RFLP) analysis. ctP3 was cloned as described in Example 2, and a subclone containing a unique sequence adjacent to the Tc1 insert isolated (pCT102). pCT102 was used as a probe to screen a genomic N2 library and identified clones were used to obtain a cosmid clone (C12G5) (courtesy J. Sulston and A. Coulson) containing sequences from the her-1 gene region. To confirm that this region included all the elements required for her-1 activity, a recessive her-1 allele was generated (hv1y101), as described in Example 3. Blots of digested genomic DNA from N2 and her-1(hv1y101) strains were screened with probes generated from fragments of cloned DNA, as described in Example 3. The probes identified a deletion in the her-1 gene in hv1y101 DNA (shown in FIG. 4B).

2. Characterization of the her-1 Transcripts

The present invention encompasses the ribonucleic acid transcription products of the her-1 gene. The identification and expression of the her-1 transcription products are described in Example 4.

Figure 4:
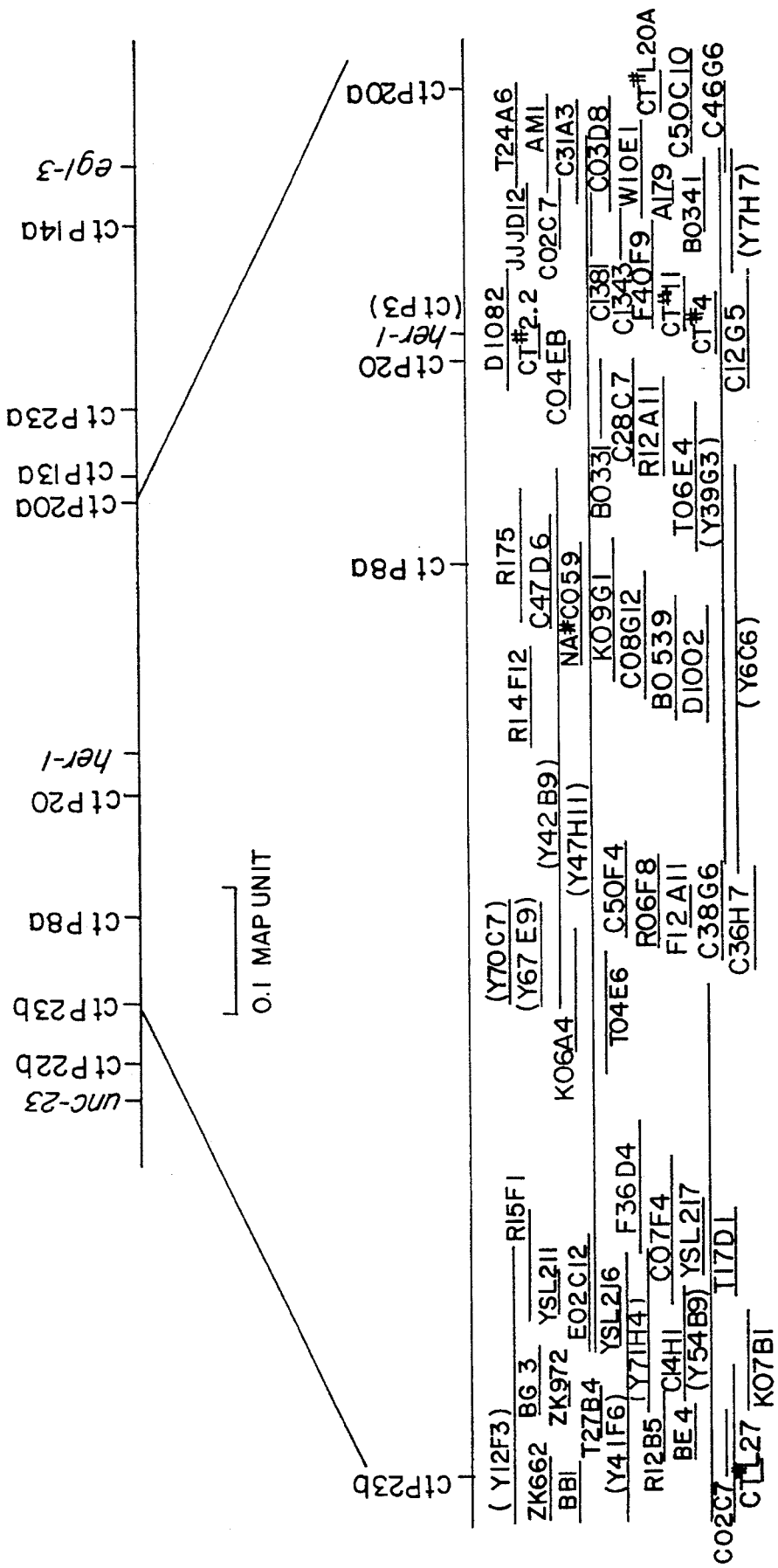
FIG. 4 and FIG. 4 (con't) compares the genetic and physical maps of the her-1 region of LG V. Only part of the her-1 contig is shown. Most of the clones indicated are cosmid clones, the remainder are YAC or lambda clones. The length of the line representing each clone is proportional to the number of HindIII sites contained in the clone.
Figure 5A:
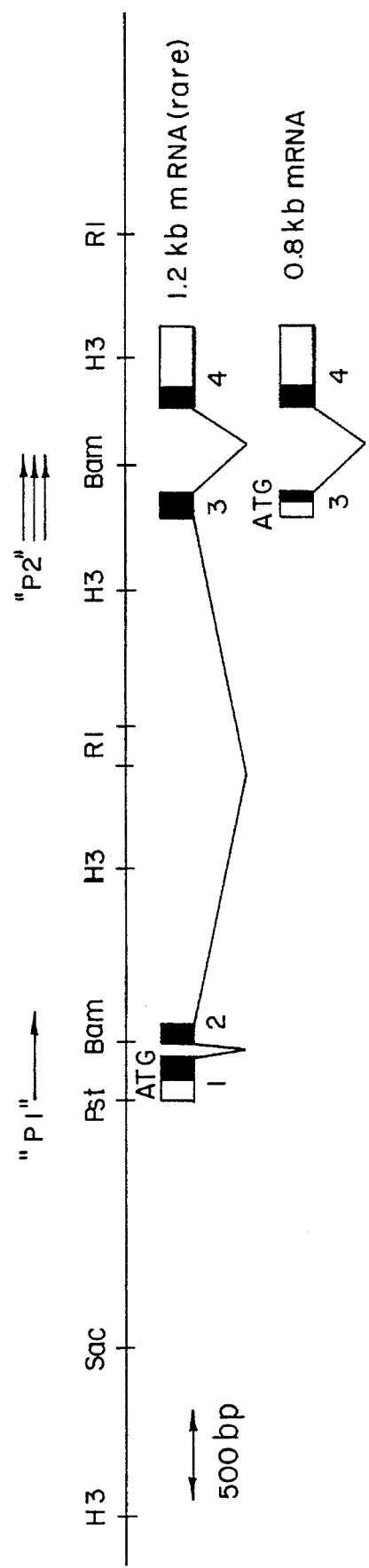

Transcribed regions of the cosmid C12G5 were initially identified as described in Example 4. Restriction fragments of cosmid DNA were labelled and used as probes on individual gel blots of RNA from N2 (XX) and him-8 (XO) embryonic (L1–L4) and adult populations. Two transcripts were identified: a 0.8 kb transcript and a 1.2 kb transcript (FIGS. 4B and 5A). The 0.8 kb transcript was relatively abundant in RNA from all developmental stages of a him-8 population (about 40% XO). Less than 1% of this level was detected in RNA from N2 embryos (about 0.2% XO) and no 0.8 kb transcript was detected in N2 animals beyond the embryo stage. The 1.2 kb transcript was only detected in the him-8 populations. Both transcripts were seen in XX animals carrying a partial loss-of-function mutation in either the sdc-1 or sdc-2 genes, indicating that these genes act to control her-1 transcript levels.

3. Sequence and Structure of the her-1 Transcripts and Characterization of the her-1 Proteins The present invention includes the description of the sequence and structure of the her-1 transcripts (FIG. 2)(SEQ ID NO:1 and SEQ ID NO:2). The invention further includes the predicted sequence of the protein products of the her-1 gene (FIG. 3)(SEQ ID NO:3 and SEQ ID NO:4). Example 5 describes the methods used to map the structures of the two her-1 transcripts as well as the cloning of cDNAs corresponding to each transcript.

The 1.2 kb transcript, characterized as described in Example 4, is predicted to encode a 175-amino acid protein. The 0.8 kb transcript is predicted to encode a 64-amino acid protein which corresponds to the C-terminal 64 amino acids of the larger protein.

The 1.2 kb transcript (FIG. 2)(SEQ ID NO:1 and SEQ ID NO:2) is initiated at the promoter designated P1 (FIG. 5A), and contains an open reading frame (ORF) of 525 bp, beginning at an ATG codon 175 bp from the 5'-end, and four exons. It is predicted to encode a 175-amino acid, cysteine-rich protein with an Mr of about 20 kDa. This ORF is spliced in-frame across all three exon-exon splice sites, and includes the ORF found in the 0.8 kb transcript (described below). This protein includes at its N-terminal end a signal sequence for secretion into the endoplasmic reticulum (ER)(von Heijne (1986) Nuc. Acids Res. 14:4683–4690)(FIGS. 2 and 3). This protein includes two potential sites for post-translational N-linked glycosylation (at sites 98 and 163)(FIG. 3)(SEQ ID NO:2), as well as four pairs of basic residues that could be sites for post-translational proteolytic processing (FIG. 2).

The 0.8 kb transcript includes a 220 bp ORF beginning at the point of trans-splicing (FIG. 2), and corresponding to exons 3 and 4 of the larger transcript. At position 77 of the smaller transcript (FIG. 3)(SEQ ID NO:4) (4023 in the genomic sequence; FIG. 2)(SEQ ID NO:2) is an ATG codon. Initiation of translation at this site would result in a protein of about 10 kDa, corresponding to the C-terminal 64 amino acids of the larger protein.

To confirm the models for exon/intron structure shown in FIG. 5, and to more precisely define the 5'-ends of each transcript, mapping experiments using RNAase protection experiments were carried out assaying both strands of DNA to detect any possible transcripts from another overlapping gene (Example 6). Protection of exon 1 and 2 probes with total RNA was detectable only after long exposures; poly A$^+$ RNA was used to obtain stronger signals. These experiments gave no evidence for other transcripts, confirmed the predicted splice sites, and revealed no additional exons in any of the predicted introns. However, they showed that both the 5'-end of exon 1 and the 3'-end of exon 4 can vary slightly in length, suggesting that promoter elements controlling the large transcript utilize multiple capping sites, and that transcriptional termination machinery processing both transcripts can choose between several poly A addition sites. RNAase protection assays of the 5'-end of exon 3 revealed a weakly protected band about 35 nucleotides longer than the exon and more abundant in total than in poly A$^+$ RNA preparations support the existence of a second promoter, designated P2, just upstream of the acceptor splice junction of exon 3 (FIG. 5A).

RNAase protection experiments were also used to compare levels of the two transcripts in embryos of a him-8(e1489) strain (about 40% XO), N2 (about 0.2% XO), and SP756 (about 0.02% XO), a hermaphrodite strain in which X nondisjunction is suppressed by the X-to-IV translocation mnT12 (Sigurdson et al. (1986) Mol. Gen. Genet. 202:212–218). RNA from both N2 and mnT12 embryos gave similar levels of protection with an exon-3 probe but no detectable protection of an exon-1,2 probe. These results indicate that both her-1 promoters are XO-specific: XX embryos contain no detectable 1.2 kb transcript, but do contain low levels of the 0.8 kb transcript.

4. Ectopic Expression Experiments

Central to the present invention is the discovery of the secretory nature of the her-1 protein.

Genetic experiments have been carried out to address the question of autonomy in the *C. elegans* sex determination pathway. Schedin et al. (1991) Development 112:833–879, showed that in triploid intersex mosaic animals with intermediate X/A ratios, positionally related cells tended to make non-random choices of sexual fate, consistent with influences of neighboring cells on each other. A genetic analysis of the sdc-1 gene (Villeneuve and Meyer (1990a and 1990b) supra) gave results consistent with nonautonomous action of its gene product or a gene product under its control (FIG. 1). However, the molecular characterization of the sdc-1 gene (Nonet and Meyer (1991) Nature 351:65–68) predicted that this product, implicated in negative regulation of her-1 transcription contains seven Zn$^{++}$ finger-like domains (often found in nuclear DNA binding proteins), suggesting that sdc-1 is likely to play a role in transcriptional control and unlikely to act cell nonautonomously itself. Mosaic analysis of the terminal regulatory gene tra-1 (Hunter and Wood (1990) Cell 63:1193–1204), the product of which is also likely to be a transcription factor (Hodgkin (1991) Neuron 6:177–185), showed that its function in specifying hermaphrodite fates is completely cell-autonomous. Therefore, any non-autonomy in the pathway of FIG. 1 must reside upstream of tra-1 and downstream of sdc-1. The available information on the molecular structures of tra-2, fem-1, and fem-3 indicates that none of these are likely to be secreted proteins. Ectopic expression experiments were conducted to determine whether either of the two predicted her-1 encoded proteins is secreted. Specifically, the experiments described in Example 7 were directed at determining whether either transcript in one cell type (body-wall muscle) could affect sex determination of other tissues.

cDNAs of the 1.2 kb and 0.8 kb transcripts were subcloned into an expression vector containing an enhancer, promoter, and poly A addition signal from the unc-54 gene (Fire et al. (1990) Gene 93:189–198), the major body wall muscle myosin protein expressed only in muscle cells. In worms transformed with a lacZ fusion construct driven by the unc-54 enhancer-promoter combination, β-galactosidase activity is detected only in the muscle cells (Fire et al. (1990) supra, and Experiment 7). Further, constructs carrying the smaller her-1 cDNA had no masculinizing effect in the ectopic expression experiments. However, all progeny of worms transformed with a plasmid carrying the cDNA of the 1.2 kb transcript were masculinized, establishing that the 1.2 kb transcript encodes biologically active her-1 product and can function non-autonomously to masculinize cells that do not produce it.

A further experiment was conducted to examine the ability of the her-1 signal sequence to function in cis to target a heterologous protein for secretion (Example 7). The N-terminal 58 amino acids of the larger her-1 polypeptide was fused to a modified *E. coli* β-galactosidase. Since secretion of β-galactosidase will inactivate its activity (Silhavy and Beckwith (1985) Microbiol. Rev. 49:398–418), a lacZ expression vector was used (Fire et al. (1990) supra) containing a synthetic trans-membrane domain, which prevents translocation of the enzyme into the ER. When this modified enzyme is expressed, it remains tethered to the cytoplasmic face of the ER, golgi apparatus, and plasma membrane. Animals expressing the her-1-lacZ fusion protein driven by the unc-54 enhancer and promoter showed strong staining of these organelles in body muscle cells after fixation and histochemical staining with the X-gal.

The experiments described in Example 7 confirm that the her-1 protein is a secretory protein involved in cell-cell interactions that result in non-autonomous sex determination in *C. elegans*. The most likely target of her-1 action is the tra-2 gene (FIG. 1). Okkema and Kimble (1991) EMBO J. 10:171–176, have cloned tra-2 and shown that the steady-state levels of the major transcripts are 15-fold lower in males than in hermaphrodites. The major somatic product of the tra-2 gene is a large protein with an apparent signal sequence and several other hydrophobic domains capable of spanning the plasma membrane. The tra-2 product may be a receptor, inhibited by direct binding of the her-1 ligand.

5. Gene Expression

In one embodiment of the present invention, the her-1 nucleic acid sequence may be used to establish recombinant expression systems for manufacture of biologically active her-1 protein. In a preferred version of this embodiment, expression may occur in a microorganism, in particular *Escherichia coli*, as described in Example 8. Expression may also occur in a mammalian cell as described in Example 9. The her-1 protein may also be produced by expression in other expression systems, including microbial and baculovirus expression systems.

The her-1 gene may be modified to facilitate efficient expression in *E. coli*. Such modifications, described in more detail below, may include, but are not limited to, the following: (i) preparation of a DNA sequence that encodes only the inferred mature (processed) form of the protein, by removal of additional coding and non-coding sequences that may be present in the gene; (ii) alterations of nematode codons to those used preferentially by *E. coli*; (iii) addition of a translational coupler to promote efficient translation in *E. coli*; (iv) insertion of new restriction sites for convenience of subsequent ligation and cloning; and (v) insertion of the DNA into one or more of several expression vectors designed to promote efficient expression of the DNA in *E. coli*. The final expression constructs may be transformed into a suitable strain of *E. coli* and transformants producing mature her-1 protein selected for scale-up and manufacture.

A. General

A natural or synthetic DNA sequence may be used to direct production of her-1 protein. The general expression method comprises:

1. preparation of a DNA sequence capable of directing a host cell to produce a protein having her-1 activity or a precursor thereof;
2. cloning the DNA sequence into a vector capable of being transferred into and replicated in a host cell, such vector containing operational elements needed to express the DNA sequence or precursor thereof;
3. transferring the vector containing the synthetic DNA sequence and operational elements into a host cell capable of expressing the DNA encoding the her-1 protein or a precursor thereof;
4. culturing the host cells under the conditions for amplification of the vector and expression of the protein or precursor thereof;
5. harvesting the protein or a precursor thereof; and
6. purifying the protein or a precursor thereof.

B. DNA Sequences

DNA sequences contemplated for use in this method are discussed in part in Example 5. FIG. 2 (SEQ ID NO:1 and SEQ ID NO:2) sets forth the nucleic acid sequence coding for the her-1 proteins. It is contemplated that these sequences include synthetic and natural DNA sequences and combinations thereof. The natural sequences further include cDNA or genomic DNA segments.

The means for synthetic creation of polynucleotide sequences encoding a protein identical to that encoded by the cDNA or genomic polynucleotide sequences are generally known to one of ordinary skill in the art, particularly in light of the teachings contained herein. As an example of the current state of the art relating to polynucleotide synthesis, one is directed to Matteucci, M. D., and Caruthers, M. H., in J. Am. Chem. Soc. 103:3185 (1981) and Beaucage, S. L. and Caruthers, M. H. in Tetrahedron Lett. 22:1859 (1981), and to the instructions supplied with an ABI oligonucleotide synthesizer, each of which is specifically incorporated herein by reference.

These synthetic sequences may be identical to the natural sequences shown in FIG. 2, or they may contain different nucleotides. In one embodiment, if the synthetic sequences contain nucleotides different from those found in the natural DNA sequences of this invention, it is contemplated that these different sequences will still encode a polypeptide which has the same or substantially the same primary structure as the her-1 protein described herein. In an alternate embodiment, the synthetic sequence containing different nucleotides will encode a polypeptide which has the same biological activity as the her-1 protein described herein.

Additionally, the DNA sequence may be a fragment of a natural sequence, i.e., a fragment of a polynucleotide which occurred in nature and which has been isolated and purified for the first time by the present inventors. In one embodiment, the DNA sequence is a restriction fragment isolated from a cDNA library.

In an alternative embodiment, the DNA sequence is isolated from a nematode genomic library. Nematode cDNA libraries and genomic libraries may be probed with at least one probe capable of binding to the her-1 gene or its gene product. After identification of the gene coding for the protein by virtue of its ability to bind to the probe, the gene may be isolated and linked to operational elements necessary to maintain and express the gene in a host cell.

C. Vectors (i) Microorganisms, especially *E. coli*

The vectors contemplated for use in the present invention include any vectors into which a DNA sequence as discussed above can be inserted, along with any preferred or required operational elements, and which vector can then be subsequently transferred into a host cell and replicated in such cell. In particular, it is preferred that all of these vectors have some or all of the following characteristics: (1) possess a minimal number of host-organism sequences; (2) be stably maintained and propagated in the desired host; (3) be capable of existing in a high copy number in the desired host; (4) possess a regulatable promoter positioned so as to promote transcription of the gene of interest; (5) have at least one marker DNA sequence coding for a selectable trait present on a portion of the plasmid separate from that where the DNA sequence will be inserted; and (6) have a DNA sequence capable of terminating transcription.

The cloning vectors of the present invention contain various operational elements. These "operational elements" include the following: regulators, promoters, transcription terminator, non-translated sequence, ribosome binding sites, leader sequence and translational coupler, translation terminator, selectable marker. In practice, it is possible to construct these vectors in a way that allows them to be easily isolated, assembled and interchanged.

The operational elements as discussed herein are routinely selected by those of ordinary skill in the art in light of prior literature and the teachings contained herein. General examples of these operational elements are set forth in B. Lewin, *Genes*, Wiley & Sons, New York (1983), which is specifically incorporated herein by reference. Various examples of suitable operational elements may be found on the vectors discussed above and may be elucidated through review of publications discussing the basic characteristics of the aforementioned vectors.

Upon synthesis and isolation of all necessary and desired component parts of the above-discussed vector, the vector is assembled by methods generally known to those of ordinary skill in the art. Assembly of such vectors is believed to be within the duties and tasks performed by those of ordinary skill in the art and, as such, is capable of being performed without undue experimentation. For example, similar DNA sequences have been ligated into appropriate cloning vectors, as set forth in Maniatis et al. (1982) in *Molecular Cloning: A Laboratory Manual* (Cold Spring Harbor Laboratory: Cold Spring Harbor, N.Y.), which is specifically incorporated herein by reference.

In construction of the cloning vectors of the present invention, it should additionally be noted that multiple copies of the DNA sequence and its attendant operational elements may be inserted into each vector. In such an embodiment, the host organism would produce greater amounts per vector of the desired her-1 protein. The number of multiple copies of the DNA sequence which may be inserted into the vector is limited only by the ability of the resultant vector, due to its size, to be transferred into and replicated and transcribed in an appropriate host cell.

(ii) Other Microorganisms

Vectors suitable for use in microorganisms other than *E. coli* are also contemplated for this invention. The microorganism vectors described herein are routinely employed by those of ordinary skill in the art in light of prior literature and the teachings contained herein. Assembly of such vectors is believed to be within the duties and tasks performed by those with ordinary skill in the art and, as such, is capable of being performed without undue experimentation.

(a) Pseudomonas Vectors

Several vector plasmids which autonomously replicate in a broad range of Gram negative bacteria are preferred for use as cloning vehicles in hosts of the genus Pseudomonas. Certain of these are described by Tait, R. C., Close, T. J., Lundquist, R. C., Hagiya, M., Rodriguez, R. L., and Kado, C. I. in Biotechnology, May 1983, pp. 269–275; Panopoulos, N.J. (1981) in *Genetic Engineering in the Plant Sciences* (Praeger Publishers, New York, N.Y.), pp. 163–185; and Sakagucki (1982) Current Topics in Microbiology and Immunology 96:31–45, each of which is specifically incorporated herein by reference.

(b) Bacillus Vectors

A preferred expression system in hosts of the genus Bacillus involves using plasmid pUB110 as the cloning vehicle. As in other host vector systems, it is possible in Bacillus to express the her-1 protein of the present invention as either an intracellular or a secreted protein. Shuttle vectors that replicate in both Bacillus and *E. coli* are available for constructing and testing various genes as described by Dubnau, D., Gryczan, T., Contente, S., and Shivakumar, A. G. (1980) in *Genetic Engineering*, Vol. 2, Setlow and Hollander, eds. (Plenum Press, New York, N.Y.), pp. 115–131, specifically incorporated herein by reference.

(iii) Yeast vectors

Maintenance of foreign DNA introduced into yeast can be effected in several ways as described by Botstein, D. and Davis, R. W. (1982) in *The Molecular Biology of the Yeast Saccharomyces*, Strathern, Jones and Broach, eds. (Cold Spring Harbor Laboratory: Cold Spring Harbor, N.Y.), pps. 607–636, specifically incorporated herein by reference. One preferred expression system for use with host organisms of the genus Saccharomyces harbors the cDNA of the 1.2 kb her-1 transcript on the 2 micron plasmid. The advantages of the 2 micron circle include relatively high copy number and stability when introduced into cir' strains. These vectors preferably incorporate the replication origin and at least one antibiotic resistance marker from pBR322 to allow replication and selection in *E. coli*. In addition, the plasmid will preferably have the 2 micron sequence and the yeast LEU2 gene to serve the same purposes in LEU2 defective mutants of yeast.

If it is contemplated that the her-1 protein will ultimately be expressed in yeast, it is preferred that the cloning vector first be transferred into *E. coli*, where the vector would be allowed to replicate and from which the vector would be obtained and purified after amplification. The vector would then be transferred into the yeast for ultimate expression of the protein.

(iv) Mammalian vectors

The cDNA for the 1.2 kb her-1 transcript will serve as the gene for expression of the protein in mammalian cells. It should have a sequence that will be efficient at binding ribosomes such as that described by Kozak (1987) in Nucleic Acids Res. 15:8125–8132, specifically incorporated herein by reference, and should have coding capacity for a leader sequence to direct the mature protein out of the cell in a processed form. The DNA restriction fragment carrying the complete cDNA sequence can be inserted into an expression vector which has a transcriptional promoter and a transcriptional enhancer as described by Guarente (1988) Cell 52:303–305 and Kadonaga et al. (1987) Cell 51:1079–1090, both of which are specifically incorporated herein by reference. The promoter may be regulatable as in the plasmid pMSG (Pharmacia Cat. No. 27450601) if constitutive expression of the protein is harmful to cell growth. The vector should have a complete polyadenylation signal as described by Ausubel et al. (1987) in *Current Protocols in Molecular Biology*, Wiley, specifically incorporated herein by reference, so that the mRNA transcribed from this vector is processed properly. Finally, the vector will have the replication origin and at least one antibiotic resistance marker from pBR322 to allow replication and selection in *E. coli*.

In order to select a stable cell line that produces the her-1 protein, the expression vector can carry the gene for a selectable marker such as a drug resistance marker or carry a complementary gene for a deficient cell line, such as a dihydrofolate reductase (dhfr) gene for transforming a dhfr(−) cell line as described by Ausubel et al., supra. Alternatively, a separate plasmid carrying the selectable marker can be cotransformed along with the expression vector. In one preferred embodiment of the present invention, the cDNA corresponding to the 1.2 kb her-1 transcript is subcloned into the plasmid vector pSG5 (Green et al. (1988) Nucl. Acids Res. 16: 369, specifically incorporated herein by reference) which is designed for transient expression of cloned genes in cells expressing SV40 T antigen, such as COS cells (Example 9).

(v) Insect vectors

Biologically active her-1 can be expressed in a baculovirus system by construction of a chimeric gene consisting of the 1.2 kb her-1 cDNA sequence linked to the polyhedrin promoter and leader sequence of baculovirus DNA. Examples of plasmids carrying the promoter and leader sequence for baculoviral DNA include pAcYM1 (Bishop (1987) J. Gen. Virol. 68:1233), pAC101 (U.S. Pat. No. 4,745,501), pac373 (Smith (1985) Proc. Natl. Acad. Sci. USA 82:8404), and pEV51 (Rice (1987) J. Virol. 61:1712).

The her-1 cDNA sequence is inserted into a baculovirus cloning vector providing the appropriate regulatory functions required for the efficient transcription, translation, and processing of the coding sequence. The baculovirus expression system utilizes a polyhedrin promoter which can direct expression of the her-1 gene.

D. Host Cells/Transformation

Once assembled, the vectors of the present invention are transferred into an appropriate host cell. These host cells may be microorganisms, insect cells or mammalian cells. In the preferred embodiment of this invention, the host cells utilized are microorganisms, and more specifically are *E. coli* cells.

(i) Microorganisms

It is believed that any microorganism having the ability to take up exogenous DNA and express those genes and attendant operational elements may be chosen. After a host organism has been chosen, the vector is transferred into the host organism using methods generally known to those of ordinary skill in the art. See in general Sambrook et al. (1989) *Molecular Cloning: A Laboratory Manual*, 2d ed. (Cold Spring Harbor Laboratory: Cold Spring Harbor, N.Y.) and Davis et al. (1980) in *Advanced Bacterial Genetics* (Cold Spring Harbor Laboratory: Cold Spring Harbor, N.Y.), both of which are specifically incorporated herein by reference.

It is preferred that the host microorganism be a facultative anaerobe or an aerobe. Particular hosts which may be preferable for use in this method include yeast and bacteria. Specific yeasts include those of the genus Saccaromyces, and especially *Saccharomyces cerevisiae*. Specific bacteria include those of the genera Bacillus, Escherichia, and Pseudomonas, especially *Bacillus subtilis* and *Escherichia coli*. Example 8 describes a preferred method of expressing the her-1 protein in an *E. coli* expression system.

(ii) Mammalian Cells

The vector can be introduced into mammalian cells in culture by several techniques such as calcium phosphate: DNA coprecipitation, electroporation, microinjection, or protoplast fusion. One preferred method is coprecipitation with calcium phosphate as described by Ausubel et al. (1987), supra.

Many stable cell types exist that are transformable and capable of transcribing and translating the cDNA sequence, processing the precursor her-1 protein and secreting the mature protein. However, cell types may be variable with regard to glycosylation of secreted proteins and post-translational modification of amino acid residues, if any. Thus, the ideal cell types are those that produce a recombinant her-1 protein identical to the natural molecule. Example 9 describes a preferred method of producing the her-1 protein in a COS cell system.

(iii) Insect cells

The vector can be introduced into an appropriate host cell, such as *Spodoptera frugiperda*, to result in expression of a biologically active her-1 protein. Techniques for introduction of the vector into the host cell include viral transfection, DEAE-dextran induced pinocytosis, particle acceleration, or calcium phosphate precipitation. The preferred method is coprecipitation with calcium phosphate as described by Ausubel et al. (1987), supra. Example 10 describes a preferred method of expressing the her-1 protein in an insect expression system.

E. Culturing Engineered Cells

The host cells are cultured under conditions appropriate for the expression of the her-1 protein. These conditions are generally specific for the host cell, and are readily determined by one of ordinary skill in the art in light of the published literature regarding the growth conditions for such cells and the teachings contained herein. For example, Bergey's Manual of Determinative Bacteriology, 8th ed., Williams & Wilkins Company, Baltimore, Md., which is specifically incorporated herein by reference, contains information on conditions for culturing bacteria. Similar information on culturing mammalian cells may be obtained from Pollack, R. (1975) in *Mammalian Cell Culture* (Cold Spring Harbor Laboratory: Cold Spring Harbor, N.Y.), specifically incorporated herein by reference.

F. Renaturing of Expressed Recombinant Proteins

In the event that the harvested her-1 protein is not fully biologically active, the harvested protein may be maintained under conditions to allow the her-1 protein to assume its active tertiary structure according to standard procedures (for example, Kohno et al. (1990) Methods Enzymol. 185:187).

In one embodiment of the present invention, the recombinant mature her-1 protein is purified subsequent to harvesting and prior to assumption of its active structure. In an alternate embodiment, the her-1 protein may be allowed to refold to assume its active structure prior to purification. In yet another embodiment, the protein is present in its refolded, active state upon recovery from the culturing medium.

In certain circumstances, the mature her-1 protein will assume its proper, active structure upon expression in the host microorganism and transport of the protein through the cell wall or membrane or into the periplasmic space. This will generally occur if DNA coding for an appropriate leader sequence is linked to the DNA sequence coding for the recombinant protein.

In one embodiment of the present invention, the protein produced in microorganisms may lack substantial biological activity and will need to be refolded and renatured to provide a biologically active her-1 protein.

Often the lack of biological activity in proteins expressed in microorganisms is related to improper formation of intramolecular disulfide bonds. In a preferred version of this embodiment, the recombinant her-1 protein produced in *E. coli* may be refolded and renatured to attain the correct configuration of intramolecular disulfide bonds as well as biological activity.

In a preferred version, the recombinant protein may be refolded and renatured by using the following steps:

(1) Any intramolecular or intermolecular disulfide bonds and/or any noncovalent interactions which have occurred involving the mature her-1 protein produced in a microorganism are first disrupted. In order to do this, the protein is exposed to sufficient denaturant (for example, guanidine hydrochloride or urea) and sufficient reducing agent (for example, beta-mercaptoethanol, dithiothreitol, or cysteine) to denature the protein, disrupt noncovalent interactions, and reduce disulfide bonds.

(2) After the mature her-1 protein has been denatured and reduced, the free thiols present in the reduced protein are oxidized by addition of a large excess of disulfide-containing reagent (for example, glutathione or cystine). This reaction produces mixed disulfide bonds in which each cysteine residue in the mature protein forms a disulfide bond with the monomeric form of the oxidizing agent. This step helps to prevent the formation of incorrect intramolecular disulfide bonds in the her-1 protein during subsequent processing.

(3) The denaturant and oxidizing agent are then diluted to a defined concentration and a thiol-containing reagent (for example, cysteine) is added to catalyze disulfide interchange. The objective is to produce an environment in which the denaturant concentration is sufficiently reduced to allow the protein to assume various 3-dimensional configurations and in which the oxidation/reduction potential is adjusted to allow the formation and breaking of disulfide bonds. It is presumed that the proper 3-dimensional structure and disulfide bonding pattern of the mature protein is energetically more stable than other possible configurations. Therefore, conditions in which the her-1 protein is allowed to assume a variety of 3-dimensional conformations and intramolecular disulfide bond patterns, will allow a significant proportion of the her-1 protein to reform the correct intramolecular disulfide bonding pattern, the correct 3-dimensional structure, and, therefore, to become biologically active.

G. Purification of Recombinant her-1 Protein

The her-1 protein may be purified from extracts of the expression host cell by standard techniques of protein chemistry until the recombinant protein is sufficiently pure to be used for its intended use, either in pharmaceutical, veterinary, or pesticidal applications. Pharmaceutical purity is defined as at least 90% of all proteins in the preparation being the her-1 protein, and preferably at least 95% of all the protein being the her-1 protein. In a preferred embodiment the procedures to be used for purification of the recombinant protein may include, but are not limited to, some or all of the following: ion exchange chromatography (e.g., Q-. S-, and DEAE-Sepharose ion exchange columns), gel permeation chromatography, (e.g., Superose sizing columns), chromatofocusing (e.g., Mono-P columns), hydrophobic interaction chromatography (e.g., octyl- and phenyl-Sepharose HIC columns), affinity chromatography (e.g., zinc, copper, and mercury metal-affinity columns).

6. Expression of her-1 in Soil and Ruminant Bacteria

This invention encompasses transformation of soil and ruminant bacteria with her-1 DNA or cDNA coding for the her-1 protein such that the her-1 protein is constitutively or transiently expressed in the soil and ruminant bacteria. Also included in this invention is transformation of soil and ruminant bacteria with DNA or cDNA of other nematode species which is equivalent to the protein product of the her-1 gene of *C. elegans* in terms of its ability to dictate male development and prevent female development.

The rhizosphere is the area of the soil surrounding the plant roots that is particularly abundant with life forms. Rhizobacteria are bacteria adapted to the rhizosphere. One approach to the control of nematode infestation of plants is to genetically engineer bacteria, in particular rhizobacteria (including Pseudomonas, Agrobacterium, Enterobacter, and Alcaligenes) (see Suslow (1982) in *Phytopathogenic Prokaryotes*, Mount and Lacy, eds., pp. 187–223), to express the her-1 protein. These bacteria can be used to introduce the her-1 protein into the immediate environment, thereby providing a means of inhibiting nematode infestation of nematode-susceptible plants. Novel bacterial cells can be engineered to produce the her-1 protein constitutively or transiently by methods known to those skilled in the art, including the use of appropriate recombinant vectors, as discussed above.

The present invention provides a means to introduce the capacity to produce the her-1 protein into the soil rhizosphere, thereby providing a means of controlling nematodes (Example 11).

This invention can also be utilized to transform ruminant bacteria with nucleic acid sequences coding for the her-1 protein. Ruminant animals can then be inoculated with the engineered bacteria which are maintained in the rumen where the her-1 protein is expressed.

7. Expression of her-1 Protein in Plant Roots By Infection with Endophytic Fungus Endophytes are fungi that live inside plant tissue (Petrini (1986) in Microbiology of the Phyllosphere, N. J. Fokkema and J. Van Den Hevel, eds. (Cambridge University Press, Cambridge, U.K.), pp. 175–187). For example, vesicular-arbuscular (VA) mycorrhizas penetrate plant tissue upon infection, forming parasitic intracellular hyphae. Although endophytic infection of some plants is known to have a toxic effect on animals and humans (Clay (1988) Ecology 69:10–16), the presence of endophytes may provide benefits to the plant such as increased survival and improved plant growth (Khan (1986) in Microbiology of the Phyllosphere, N.J. Fokkema and J. Van Den Hevel, eds. (Cambridge University Press, Cambridge, U.K.), pp. 419–435). Some of these beneficial effects are thought to result from enhanced resistance to soil-borne nematodes (West et al. (1988) Plant and Soil 112:3–6). Further, endophytes are thought to protect grasses against insect herivibores. The basis of this insect resistance appears to be alkaloids produced in the plant by the endophytes (Clay (1988) supra).

Endophytes are known to infect a wide variety of host plants, including those susceptible to nematode infestation such as soybean (Ross (1971) Phytopathology 61:1400–1403) and maize (Gerdeman (1964) Mycologia 56:342–349). One preferred way to confer nematode resistance to nematode-susceptible plants, described in Example 12, is to infect plant roots with endophytic fungi genetically engineered to express the her-1 protein. The developing embryos and larvae of nematodes attacking the plant root will be exposed to the her-1 protein produced in the plant root by the endophytes, resulting in development of male nematodes and subsequent end of the infection.

8. Expression of her-1 Protein By Plants and Plant Cells

This invention encompasses methods for transforming plants with a recombinant molecule such that the plants are capable of expressing the her-1 protein. As used herein, "plants" includes plants, plant cells, and plant tissues.

The methodology for engineering plant cells is well established (see, Nester et al. (1984) Ann. Rev. Plant Physiol. 35:387–399). Transformation of plants, plant cells, and plant tissues with foreign DNA can be achieved by any means known to the art, including transformation (Paszkowski et al. (1984) EMBO J. 3:2717–2722), electroporation (Fromm et al. (1985) Proc. Natl. Acad. Sci. USA 82:5824–5828), microinjection (Crossway et al. (1986) Mol. Gen. Genet. 202:179–185), or T-DNA mediated transfer from *Agrobacterium tumefaciens* (An et al. (1985) EMBO J. 4:277–284; Herrara-Estrella et al. (1983) Nature 303:209–213).

The method of the invention, described in Example 13, provides a means of introducing the her-1 gene into plants susceptible to nematode infection, wherein the plant is induced to express and produce the her-1 protein. In a preferred embodiment of this invention, described in Example 13, soybean plants genetically engineered to express the her-1 protein are generated by direct introduction of the cDNA of the 1.2 kb her-1 transcript into meristems of immature soybean seeds by particle acceleration, as described by McCabe et al. (1988) Bio/Technology 6:923–926, specifically incorporated herein by reference. In another embodiment of this invention, transgenic soybean plants expressing the her-1 protein are generated using Agrobacterium-mediated DNA transfer, as described by Hinchee et al. (1988) Bio/Technology 6:915–922, specifically incorporated herein by reference.

9. Method of Directly Applying the her-1 Protein to Control Nematodes

The method of the invention also includes direct application of the her-1 protein, or mimetic molecules having the equivalent biological action, to soil, plants, and animals, as a means of controlling nematodes. Example 14 describes a preferred method of directly using the her-1 protein as a means of controlling nematode infestation of plants, animals, and humans.

10. Pharmaceutical and Veterinary Compositions

In a preferred embodiment of the present invention, a therapeutic composition comprising her-1 protein or mimetic molecule is administered in an effective amount to animals and humans suffering nematode infestation.

The therapeutic composition of the present invention may be administered in a number of ways, including parenterally by injection or slow-release formulations, and orally active formulations. One preferred vehicle is physiological saline solution, but it is contemplated that other pharmaceutically acceptable carriers may be used. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Such excipients are those substances usually and customarily employed to formulate dosages for parenteral administration in either unit dose or multidose form or for direct infusion by continuous or periodic infusion from an implanted pump.

It is also contemplated that certain formulations containing her-1 protein or mimetic molecules are to be administered orally. Preferably, her-1 which is administered in this fashion is encapsulated. The encapsulated her-1 may be formulated with or without those carriers customarily used in the compounding of solid dosage forms.

Regardless of the manner of administration, the specific dose is calculated according to the approximate body weight of the person or animal to be treated, by means known to those of ordinary skill in the art.

EXAMPLE 1

C. elegans Strains and Culture

Techniques for growing and handling *C. elegans* have been described previously by Brenner (1974) Genetics 77:71–94 and Sulston and Hodgkin (1988) In: The Nematode *Caenorhabditis elegans*, W. B. Wood, ed. (Cold Spring Harbor Laboratory: Cold Spring Harbor, N.Y.), pp. 587–606, both of which are specifically incorporated herein by reference. Large scale cultures were grown on "hard" NGM plates (2.5% agar) seeded with concentrated *Escherichia coli* (strain OP50) or in liquid culture as described by Sulston and Hodgkin (1988) supra. Embryo populations were obtained by hypochlorite treatment of mixed-stage populations (Emmons et al. (1979) Proc. Natl. Acad. Sci. USA 76:1333–1337). Synchronized populations of L1 larvae were obtained by letting such embryo preparations hatch in the absence of a food supply. The percentage of male animals in any given embryo or larval population was determined by counting the number of males in an adult population grown from a small portion of the worms harvested. Pure populations of adult males were obtained by filtration (Sulston and Hodgkin (1988) supra).

General techniques for genetic analysis of *C. elegans* have been described by Brenner (1974) supra, and Herman (1988) In: The Nematode *Caenorhabditis elegans*, W. B. Wood, ed. (Cold Spring Harbor Laboratory: Cold Spring Harbor, N.Y.), pp. 17–45, both of which are specifically incorporated herein by reference. Wild-type strains used were the standard laboratory varieties Bristol N2 (Brenner (1974) supra), Bergerac EM1002 (Emmons and Yesner (1984) Cell 36:599–605), and the wild isolate DH424 (Liao et al. (1983) Proc. Natl. Acad. Sci. USA 80:3585–3589). The N2 strain was the wild-type parent of the mutant strains listed below. Characteristics of mutant phenotypes are described by Hodgkin et al. (1988) in The Nematode *Caenorhabditis elegans*, W. B. Wood, ed. (Cold Spring Harbor Press: Cold Spring Harbor, N.Y.), pp. 491–584, specifically incorporated herein by reference.

The following genes and alleles were used: Linkage group (LG) III: tra-1(e1099); LG IV: him-8(e1489); LG V: rad-4(mn158), unc-23(e25), her-1(n695ct22), e1518, e1519, e1520, e1558, e1559, e1561ts, e1564, e1574, e1807, e1821, e1914, e1917, e2296ts, n695gf, n695n826ts, n695n827, n695n830ts, n695n1100ts, y8, y10, y14, y69, y71, y101gf, y101y103, y101y104, y101y105, unc-41(e268), egl-3(n150), him-5(e1490); LG X: sdc-2(y46), sdc-1(y67ts).

EXAMPLE 2

Molecular Cloning of the her-1 Gene

The technique of "transposon-tagging" has been described by Emmons (1988) in The Nematode *Caenorhabditis elegans*, W. B. Wood, ed. (Cold Spring Harbor Press: Cold Spring Harbor, N.Y.), pp. 47–79, specifically incorporated herein by reference. General methods for the generation, preparation, and handling of recombinant DNA in plasmid, cosmid, and lambda vectors are as described in Maniatis et al. (1982) supra.

Transposon-tagging was used to isolate cloned sequences containing the her-1 gene. The *C. elegans* transposon (Tc1) is a 1.6 kb repeated sequence found in varying copy numbers in the genome of different *C. elegans* strains. Tc1 is inactive in the germline of the standard laboratory strain Bristol (Eide and Anderson (1985) Proc. Natl. Acad. Sci. USA 82:1756–1760), but a number of "mutator" strains of *C. elegans* have been generated in which Tc1 is transpositionally active in the germline, resulting in frequent spontaneous mutations (Collins et al. (1987) Nature 328:726–728).

To generate Tc1-induced alleles of the her-1 gene, use was made of the observation that introduction of a recessive her-1 mutation in cis to the n695 mutation results in reversion of the n695 phenotype to a wild-type sexual phenotype (Trent et al. (1988) supra). Insertion of Tc1 in or near the her-1 gene is expected to inactivate the her-1 gene. A strain containing the her-1 allele n695 and mutator activity from the strain TR679 was constructed by crossing a strain of genotype mut-2 (r459);her-1(n695)unc-41, TR679 males with her-1(n695) unc-41 hermaphrodites that had been outcrossed once to the Bergerac strain EM1002 (to increase the Tc1 copy number). Cross-progeny hermaphrodites were picked, and from their progeny, Unc (uncoordinated) animals saved and scored for the segregation of spontaneous unc-22 mutations and for dead eggs. These two traits were used to indicate the presence of the TR679 mutator activity. One such strain was saved and designated as BW423. BW423 was screened for spontaneous wild-type revertants no longer exhibiting the XX transformer phenotype of her-1 (n695). One of these revertant strains carried a recessive her-1 mutation, designated ct50, potentially resulting from insertion of a Tc1 element in or near the her-1 gene with inactivation of its function. ct50 was shown to be a recessive her-1 allele by the fact that the ct50n695 allele (strain designated BW451) failed to complement her-1(e1520), and failed to produce any phenotypic males when crossed with a him-8 (high incidence of males) strain.

To identify such a Tc1 element among the background of other Tc1 insertions in the genome, Tc1 polymorphisms (present in the ct50 strain and absent in Bristol) were genetically mapped with respect to the her-1 gene and two nearby flanking genes: unc-23 and egl-3 (egg laying defective) (FIG. 4A). The genetic mapping of Tc1 polymorphisms involved the following steps: (i) the number of Tc1 insertions in the background of the ct50 mutation was reduced by backcrossing BW451 five times to the wild-type Bristol strain and after each backcross reisolating the her-1(ct50n695) mutation by picking Unc-41 hermaphrodites (unc-41 is closely linked to her-1) (Trent et al. (1988) supra, and served as a tag for the ct50n695 chromosome); (ii) the resulting strain (called BW452) was used to map Tc1 polymorphisms with respect to ct50 mutations: heterozygotes of genotype her-1(ct50n695) unc-41/unc-23 egl -3 were generated, and three phenotypic classes picked from their progeny: (a) Unc-23 non-Egl, (b) Egl non-Unc-23, and (c) Unc-23 Egl hermaphrodites. Recombinant progeny (a) and (b) were made homozygous and then scored by complementation testing for the presence of the unselected her-1(ct50n695) mutation. Several independent segregants of each class were then analyzed for Tc1 polymorphisms. Unc-23 Egl hermaphrodites were used to identify Tc1 polymorphisms unlinked to the her-1 region. Genomic DNA was isolated from adults or hatched larvae using a variation of the procedure of Emmons et al. (1979) supra). DNA was digested with EcoRI, the fragments separated by electrophoresis on a 0.7% agarose gel and transferred by capillary blotting to nitrocellulose. The filter was hybridized with a $^{32}$P-labelled Tc1 probe. $^{32}$P-labelled DNA probes were prepared by nick-translation (Maniatis et al (1982) supra) or primer extension (Feinberg and Vogelstein (1983) Anal. Biochem. 132:6–13). Hybridizations were carried out in a solution of 50% formamide, 5×SSPE, 0.3% SDS and 0.1–0.2 mg/ml denatured, sheared salmon sperm DNA. By analyzing 30 independent recombinants in the unc-23 her-1 egl-3 interval, which represents less than one map unit (Trent et al. (1988) supra), the segregation of 15 Tc1 RFLPs were determined with respect to the ct50 mutation. This analysis included 14 recombination events between the unc-23 and her-1 genes and 16 between the her-1 and egl-3 genes. The 8.8 kb RFLP ctP3 segregated with the her-1 phenotype in all 30 recombinant strains. All other Tc1 polymorphisms either were unlinked or were linked to her-1 but mapped outside of the unc-23 egl-3 interval.

To clone ctP3, a partial genomic library was generated from DNA of a BW451 derivative in the plasmid vector pUC8 (Vieira and Messing (1982) Gene 19:259–268) using size-fractionated EcoRI fragments eluted from the region of an agarose gel containing the ctP3 band (and only one Bristol Tc1 band). Clones containing Tc1 sequences were identified and then subclones containing unique sequences adjacent to the Tc1 insertion were generated by EcoRV digestion and religation of the plasmid (EcoRV cuts at the extreme end of Tc1 (Rosenzweig et al. (1983) Nucleic Acids Res. 11:4201–4209). To determine which of these clones contained sequences adjacent to ctP3, blots of genomic DNA from the above describe recombinant strains were probed with the subclones and scored for the expected RFLP. A subclone (designated pCT102) containing unique sequences adjacent to ctP3 was identified, and used as a probe to screen a genomic N2 library made in the vector lambda EMBL4. Three overlapping clones were obtained covering 22 kb of genomic DNA. By comparing fingerprints of this DNA with a database generated as part of an ongoing project to obtain a complete physical map of the *C. elegans* genome (Coulson et al. (1986) Proc. Natl. Acad. Sci. USA 83:7821–7825; and (1988) Nature 335:184–186), a set (contig) of overlapping cosmid and YAC (yeast artificial chromosome) clones that included the cloned sequences from the her-1 region was identified and obtained from A. Coulson and J. Sulston. Fingerprinting methods used to identify the cosmid clone are well known in the art and described by Coulson et al, (1986) Proc. Natl. Acad. Sci. USA 83:7821–7825, specifically incorporated herein by reference.

EXAMPLE 3

Isolation of the her-1 Mutation hvly101

Mutations were induced with 1,2,3,4,-diepoxybutane (DEB; Sigma) by incubating hermaphrodites in $10^{-4}$ M DEB (0.01 ul DEB/ml M9 buffer)(Sulston and Hodgkin (1988) supra). After 3 h, the worms were washed 3 or 4 times in M9 buffer and L4 or young adults hermaphrodites were picked onto NGM plates seeded with OP50. To compare the potency of DEB to that of EMS, revertants of the dominant mutation unc-93(e1500) (Greenwald and Horvitz (1980) Genetics 96:147–164) were generated with each mutagen.

DEB produced the same frequency of wild-type revertants of el1500 as were obtained with EMS using the standard mutagenesis procedure described by Brenner (1974) supra.

The efficiency with which DEB induces small deletions in *C. elegans* was examined by generating a large number of homozygous viable unc-54 and unc-22 mutant strains (in the background of unc-105(n490), see Park and Horvitz (1986) Genetics 113:853–857), and examining genomic DNA from each strain for RFLPs on DNA blots. The deletions ranged from 0.5 to 3.5 kb in size.

The recessive her-1 mutation hv1 was generated after DEB mutagenesis of the her-1(gf) allele y101. The F1 and F2 progeny of the mutagenized hermaphrodites were scored for wild-type revertant hermaphrodites no longer exhibiting the XX transformer phenotype characteristics of y101 animals. The y101 mutation shows variable expressivity: some y101 XX animals are only weakly masculinized and are slightly abnormal, self-fertile hermaphrodites (see Trent et al. (1988) supra). A wild-type revertant strain was identified, hvly101, that was homozygous viable and failed to complement the her-1 mutation e1520.

Genomic DNA from N2 (XX) and her-1 (hvly101) strains were double-digested with BamHI and HindIII. The fragments were fractionated by electrophoresis and transferred to a nitrocellulose filter as described in Example 2. $^{32}$-P probes a–j (shown in FIG. 4B) were prepared as described below in Example 4. Eight bands were seen with the N2 digest, four of which were missing or exhibited an altered mobility in the hvly101 digest, consistent with a deletion in the her-1 gene.

EXAMPLE 4

Isolation and Expression of the her-1 Transcripts

Cosmid DNA was digested with EcoRI, HindIII, BglII and BamHi. The resulting fragments, designated a through j, and ranging in size from 0.6 to 2.5 kb (FIG. 4B), were $^{32}$P-labelled in primer extension reactions (Feinberg and Vogelstein (1983) supra) and used as probes to screen blots of embryonic RNA (total RNA and poly A$^+$ RNA) from XO and XX populations. XO animals used for these experiments were obtained from the him-8 strain which produces populations with about 40% XO animals. XO embryos and larvae cannot be separated from XX animals in large numbers, therefore, all XO-containing populations from these stages also contained about 60% XX animals. RNA was prepared as described by Meyer and Casson (1986) Cell 47:871–881, specifically incorporated herein by reference. Poly A$^+$ RNA was obtained with oligo-d(T) columns using the methods of Maniatis et al. (1982) supra. Total RNA from N2 and him-8 animals (approximately 10–30 mg per lane) was fractionated by electrophoresis on 1.4% MOPS/formaldehyde gels according to the procedure of Fourney et al. (1988) BRL Focus 10:5–7, and the RNA transferred to Zetabind (AMF Cuno) by vacuum blotting in 10×SSC. Hybridizations were carried out in a solution of 50% formamide, 5×SSPE, 0.3% SDS and 0.1–0.2 mg/ml denatured, sheared salmon sperm DNA. Probes f, g, and h identified two XO-specific transcripts: a relatively abundant 0.8 kb transcript and a less abundant 1.2 kb transcript. Probes c and d identified the 1.2 kb transcript only. Probes a, b, i and j identified transcripts that showed no sex-specificity. Probe a identified transcripts of about 1.2 and 1.6 kb; probe b also identified a transcript of about 1.4 kb but with significantly weaker signal.

Results showed that the 1.2 kb transcript is present in the mixed population of XX and XO embryos but not in XX embryos. The 0.8 kb transcript is present in both populations, but is observed in much greater quantities in XO+XX RNA than in XX RNA. Populations of XX animals (or embryos) normally contain a small fraction of XO animals, because a wild-type hermaphrodite produces about 0.2% XO self-progeny. To estimate the possible contribution of XO embryos to the observed XX level of 0.8 kb transcript, RNA blots were performed as described above in which the percentage of XO animals was carefully quantitated in the XX+XO and the XX populations. The results suggest that the low level of 0.8 kb transcription in XX embryos results primarily from contaminating XO embryos.

To investigate the expression of her-1 post-embryonically, total RNA from XO and XX animals at various stage of larval development and from adult males were examined as described above for the presence of her-1 transcripts. Both her-1 transcripts were present in all stages of him-8 (XX+ XO). The 1.2 kb transcript was not observed in XX animals at any stage of development. The 0.8 kb transcript was observed in populations of XX L1 larvae as well as embryos; this could result from contaminating XO animals in the XX populations as discussed above.

Following the methods described above, examination of total RNA from XX embryos carrying either the n695 or y101 gain-of-function her-1 alleles showed that in contrast to the N2 XX hermaphrodite embryos, n695 XX and y101 XX embryos contain relatively high levels of both the 1.2 and the 0.8 kb her-1 transcripts. These levels were estimated to be about 20-fold higher than in N2 XX embryos, but somewhat lower than the levels found in XO embryos, consistent with the observation that n695 and y101 results in only partial transformation of XX animals into males.

The effect of recessive her-1 alleles on the presence of the her-1 transcripts was examined in mixed-stage doubly mutant him; her-1 (XO+XX) hermaphrodites. Following the methods described above, both transcripts were observed in total RNA from animals carrying the following her-1 mutations: n695ct22, e1518, e1520, e1518, e1559, e1564, e1807, e1821, e2296, n695n830, y8, y14, y69, y71, y101y103, y101y104, and y105y101. In contrast, no 1.2 kb transcript was detected in total RNA from strains carrying n695ct50, e1519, e1574, n695n827, or y10. The 0.8 kb transcript was observed in these strains at approximately wild-type levels. Neither transcript was detected in him-8 her-1(y101hv1) animals. The absence of the 1.2 kb transcript in the her-1 mutant n695ct50 is consistent with the conclusion that this mutation was caused by the ctP3 Tc1 insertion event and that the 1.2 kb (but not the 0.8 kb) transcript spans or is initiated near this insertion site (FIG. 4B).

The tra-1 mutation e1099 results in an essentially complete transformation of XX animals to fertile, mating males (Hodgkin and Brenner (1977) Genetics 86:275–287). Doubly mutant strains carrying both a recessive her-1 allele and tra-1(e1099) exhibit the Tra-1 phenotype (Hodgkin (1980) Genetics 96:649–664). Total RNA from a mixed population of tra-2(e1099) XX male and tra-2(e1099); eDp6 XX hermaphrodite embryos was examined following the methods described above [the free duplication eDp6 carries a wild-type (e.g., as in N2) tra-1 allele and thus serves as a balancer for the tra-1 mutation, as described by Hodgkin (1980) supra]. Consistent with Hodgkin's prediction, the 1.2 kb her-1 transcript was undetectable, and the 0.8 kb transcript was present at a very low level similar to that seen in preparations of N2 XX embryos.

Total RNA from XX animals carrying a partial loss-of-function mutation in sdc-1 or sdc-2 was examined following the methods described above, for the presence of the her-1 transcripts. Both transcripts were found to be present at relatively high levels, consistent with the proposed role of these genes as negative regulators of the her-1 gene in XX animals (Villeneuve and Meyer (1987) supra, and (1990a) supra; Nusbaum and Meyer (1989) supra). Although the levels of the her-1 transcripts were elevated at least 20-fold as compared to N2 XX animals, they were lower than the levels observed in normal XO animals.

The direction of transcription of the sex-specific RNAs was determined using strand-specific probes from the f–h region. Strand-specific $^{32}$P RNA probes were prepared from her-1 sequences subcloned into the vector pT7/T3a-18 (Bethesda Research Laboratories). Hybridizations were carried out in the presence of 50% formamide, 5×SSPE, 0.5% SDS, 2×Denhardt's solution, 5% dextran sulfate and 0.2 mg/ml denatured, sheared salmon sperm DNA.

EXAMPLE 5

Sequencing of the her-1 Transcripts

The *C. elegans* var. Brisol (N2) mutant strains used in the experiments described in this example were as follows: LG II: rol-6(su1006); LG IV: him-8(e1489); LG V: her-1(y101hv1), (e1520). The translocation mnT12 is a fusion of chromosomes IV and X (Sigurdson et al. (1986) supra).

Total RNA was isolated from embryos using guanidinium isothiocyanate and poly A$^+$ RNA was isolated using oligo-dT-cellulose, as described by Sambrook et al. (1989) supra. Approximately 7 kb of the genomic DNA fragment shown to restore her-1 function to a hv1y101 strain (Example 3) was sequenced using chain-terminators (Sanger et al. (1977) Proc. Natl. Acad. Sci. USA 74:5463–5467) and modified T7 DNA polymerase (Sequenase 2.0, United States Biochemicals). Nested deletions for sequencing large sections of genomic DNA were generated in vivo using a Tn9-GalE system (Ahmed (1984) J. Mol. Biol. 178:941–948 and (1984) Gene 28:37–43).

The genomic DNA sequence of the sense strand was examined for significant ORFs and consensus sequences for *C. elegans* splice acceptors and splice donors (Emmons (1988) supra; Fields (1990) Nucl. Acids Res. 18:1509–1512). Four exons were identified: two in the region hybridizing to both transcripts and two in the region hybridizing only to the 1.2 kb transcript (FIG. 5A).

cDNA clones corresponding to the 0.8 kb her-1 transcript were obtained by exhaustively screening a him-8 embryonic lambda gt11 cDNA library (about 40% XO, Schauer and Wood (1990) Development 110:1303–1317), with cloned genomic DNA fragments including exons 3 and 4 (pCT111) which were $^{32}$P-labeled using random primers (Feinberg and Vogelstein (1983) supra; Benton and Davis (1977) Science 196:180–182).

cDNA clones corresponding to the 1.2 kb transcript were obtained using a modified "RACE" protocol (Frohmann et al. (1988) Proc. Natl. Acad. Sci. USA 85:8998–9002; Lob et al. (1989) Science 243:217–220). A primer complementary to the 5'-end of exon 3, JH3 (5'-CACATCTTCTTCCA-GAATCG-3') (SEQ ID NO:5), was used to prime first-strand cDNA synthesis. After tailing with terminal deoxynucleotidyl transferase and TTP, the synthesized cDNA was diluted to a volume of 500 ul, and 5 ul of that volume used as template for PCR. The upstream primer was a 9:1 mixture of MPAN-1 (5'-GGCTCGAGGTCGACTCTAGATT-3') (SEQ ID NO:6) and XbaI primer-adaptor (5'-GTCGACTCTA-GATTTTTTTTTTTTTTT-3')(SEQ ID NO:7), and the downstream primer, JH2 (5'-GAATCGTTTTGGTCGT-TGCC-3')(SEQ ID NO: 8), was an internal segment of the primer used for cDNA synthesis. Amplified fragments were rendered blunt-ended with *E. coli* DNA polymerase I (Klenow fragment). The reaction was extracted once with an equal volume of phenol-CHCl₃, precipitated with ethanol, and fractionated on a 1.2 ml spin column of Sephadex G-50. The resulting duplex cDNA was either a) ligated to an excess of phosphorylated linkers and digested with appropriate restriction enzymes, or b) digested without adding linkers before sub-cloning and DNA sequencing. Sequencing the resulting fragment confirmed the structure shown in FIG. 5A for the 1.2 kb her-1 cDNA.

EXAMPLE 6

Transcript Mapping by RNAse Protection

RNAse protection assays were performed as described by Melton et al. (1984) Nucleic Acids Res. 12:7035–7056, specifically incorporated herein by reference, and Sambrook et al. (1989) supra. Genomic fragments spanning an 8 kb region and including all the predicted exons were subcloned into the vector pT7/T3a18 containing phage T7 and T3 promoters. These were used for in vitro transcription with phage T3 or T7 RNA polymerase and $^{32}$P-α-UTP to generate asymmetric RNA probes labelled to high specific activity. To allow comparison of different assays and estimation of transcript levels, amounts of mRNA in the hybridization reactions were normalized by comparing the signal of the fragments protected by her-1 probes to those protected by a probe specific for one of the *C. elegans* actin genes, act-1.

Exons 1 and 2. Probes covering exon 2 (113 bp) [pMPE13-2 and pT3F430(EcoRV)] protected a set of bands 110–114 bases long which were not seen with probes starting further upstream (pT7H2P2)(FIG. 5C). Probes covering the 5'-end of exon 1 protected four sets of bands of approximately 175, 210, 235 and 255 bases [pMPE13-2 and pCT115(BglII)] (FIG. 5C), except the probe pT7H2P2 which yielded corresponding protected bands 55 to 70 bases smaller, suggesting multiple transcription start sites at a promoter (P1) 5' of exon 1. This interpretation was confirmed by the demonstration that an internal probe [pT3F430(EcoRV)] gave only a single, stronger set of protected bands of about 135 bases.

Exon 3. Probes covering exon 3 (158 bp) (pCT114(FokI), pT7X3, and pMP12-1)(FIG. 5C) gave a strong set of protected bands corresponding to the full-length exon (150–165 bases). In addition the probes pCT114(FokI) and pT7X3 gave a weak band of 185 bases. High resolution mapping with a shorter probe (pMP15-1) protected bands of 35 and 40 bases, but pMP17-1, which is even more 5', did not appear to give any protected bands. These data suggest that intron 2 contains a strong second promoter (P2) which drives a transcription start site 20–40 bp upstream of exon 3, and that enough unspliced RNA is present to be detected by the protection assay.

Exon 4. The probe pSPH113 (FIG. 5C) covering exon 4 (about 582 bp) gave sets of protected bands of approximately 610, 575, 525, and 490 bases. Protection of the expected corresponding sets from a smaller probe that started much closer to the AATAA sequences and ended within exon 4 (pMPN1-7-1) confirmed that all four of these sets are protected by her-1 transcripts, suggesting multiple termination and poly A addition sites.

Similar experiments were conducted with embryonic RNA from N2 (0.2% XO) and mnT12 (0.02% XO) strains. The strong bands of exons 3 and 4 seen with the RNA from him-8 were barely detectable in RNA from either N2 or mnT12. The signal from him-8 was at least 10 times stronger than that from N2 or mnT12. The fainter bands of exons 1 and 2 and the putative unspliced exon 3 were not detected above backgrounds in N2 or mnT12.

EXAMPLE 7

Ectopic Expression of the her-1 Transcripts cDNAs for the 1.2 kb and 0.8 kb transcripts (Example 5) were subcloned into the expression plasmid pPD30.38 (Fire et al. (1990) EMBO J. 5:2673–2680), containing an enhancer, promoter, and poly A addition signal from the unc-54 gene (Waterston (1988) in The Nematode *Caenorhabditis elegans*, W. B. Wood, ed. (Cold Spring Harbor Laboratory, Cold Spring Harbor, N.Y.), pp. 281–335). The unc-54 protein and its mRNA are expressed only in body muscle cells, most of which are not sexually dimorphic (Sulston et al. (1983) Dev. Biol. 100:64–119). When worms are transformed with a lacZ fusion construct driven by the unc-54 enhancer-promoter combination, β-galactosidase activity is detected only in these same muscle cells (Fire et al. (1990) supra). The ectopic expression vectors pMPW12-1 and pMPZ159 (FIG. 5B) into which her-1 cDNA fragments were inserted for muscle-specific expression were provided by A. Fire.

Transgenic worms were generated essentially as described by Mello et al. (1991) EMBO J. 10:3959–3970. Plasmid DNAs at a concentration of 100–200 ug/ml were mixed with Fire's injection buffer (minus the Lucifer Yellow)(Fire (1986) EMBO J. 5:2673–2680) and co-injected with marker rol-6(su1006) DNA into the distal syncytial gonad of young adult N2 hermaphrodites. The dominant marker rol-6(su1006) on the plasmid pRF4 was used to identify transformed animals among the F1 progeny of these P0 animals (based on their Rol phenotype). When possible, F2 Rol animals were selected to establish lines carrying heritable extrachromosomal arrays. To obtain lines with chromosomally integrated constructs, young adult hermaphrodites carrying an array were subjected to gamma-irradiation (3800 rad), distributed to individual plates and screened for production of 60%–75% Rol F2 progeny (integrated constructs often show incomplete penetrance of the dominant Rol phenotype), indicating Mendelian transmission of the rol-6 marker (Krause et al. (1990) Cell 63:907–919).

All resulting Rol animals were masculinized, ranging from egg-laying-defective (Egl) hermaphrodites with slightly truncated tails to animals of male size and shape, with male gonads containing only sperm and distinctly masculinized tails. The strongly transformed animals did not produce vitellogenin, indicating that the intestine was also transformed. When the same construct was injected into him-8(e1489);her-1(y101hv1) hermaphrodites, transformed animals produced apparently complete male progeny (presumably XO).

To examine the ability of the her-1 signal sequence to function in cis to target a heterologous protein for secretion, a vector was constructed using the above-described techniques, comprising the N-terminal 58 amino acids of the larger her-1 protein fused to a modified *E. coli* β-galactosidase (pMPZ181)(FIG. 5B), and a lacZ expression plasmid (Fire et al. (1990) supra) containing a synthetic transmembrane domain. Populations of animals containing lacZ fusions were grown on Lac⁻ bacteria, harvested, and frozen in 2% paraformaldehyde, 0.01% glutaraldehyde on dry ice for 5 min. After rapid thawing and rinsing in PBS, the fixed animals were immersed in cold acetone for a further 5 min, air dried and then stained with X-gal for 4–24 hrs at 16° C.–37° C., as described by Fire et al. (1990) supra. Phalloidin staining of muscle actin bundles was carried out as described by Waterson et al. (1984) supra; rhodamine-conjugated phalloidin (Molecular Probes, Eugene, OR) was diluted 1:20 with PBS before use.

Animals expressing the her-1 lacZ fusion protein showed strong staining in the ER, golgi apparatus, and plasmid membrane of body muscle cells after fixation and histochemical staining with X-gal. The tissue specificity of the unc-54 promoter in these constructs was confirmed with rhodamine-conjugated phallodin staining, a fungal toxin specific for actin bundles (Wieland et al. (1983) Int. J. Pept. Protein Res. 21:3–10).

EXAMPLE 8

Expression of her-1 in *E. coli*

A number of expression vectors are available for expression of the her-1 protein in *E. coli*. In one embodiment of the present invention, the cDNA of the 1.2 kb her-1 transcript is ligated into a pET vector containing the bacteriophage T7 promoter inserted into a pBR322 plasmid, as described by Studier et al. (1990) Methods Enzymol. 185:60–89, specifically incorporated herein by reference. The recombinant vector is introduced into *E. coli* and expression initiated by delivery of T7 RNA polymerase to the cell by induction or infection (Studier et al. (1990) supra). Cells are harvested after sufficient time for substantial accumulation of her-1 protein has occurred, and the her-1 protein purified by methods known to the art, as discussed above.

In another embodiment of the invention, a vector is constructed utilizing the tryptophan operon (trp) promoter of *E. coli*, as described by Yansura and Henner (1990) Methods Enzymol. 185:54–60, specifically incorporated herein by reference. The cDNA of the 1.2 kb her-1 transcript is placed under control of the trp promoter, and the vector introduced into an *E. coli* strain. The trp promoter is induced by starvation of the *E. coli* culture for tryptophan, thereby initiating synthesis of the her-1 protein. Cells are harvested after sufficient time for substantial accumulation of her-1 protein has occurred, and the her-1 protein purified by methods known to the art, as discussed above.

EXAMPLE 9

Expression of her-1 in COS Monkey Cells

Plasmids containing the SV40 origin of replication provide a means of obtaining a high-level of transient expression of her-1 protein in COS cells (Glutzman (1981) Cell 23:175). The cDNA of the 1.2 kb her-1 transcript (Example 5) is inserted into an SV40 recombinant vector such as pMT2 as described by Kaufman (1990) Methods Enzymol. 185:487–511, specifically incorporated herein by reference, or pSG5 (Green et al. (1988) supra). This DNA is transfected into COS-7 cells by the method of Sompayrac and Danna (1981) Proc. Natl. Acad. Sci. USA 78:7575–7578. COS-7 cells are subcultured 1:6 into 100 mM tissue culture plates 24 hrs before transfection. Per 100 mm culture plate, 30 ug lipofectin and 0.3–1 ug plasmid DNA are used. After transfecting for 24 hrs, the medium is aspirated off and replaced with OptiMEM I+3% fetal calf serum (FCS). After 48 hrs, the medium and/or cultures are harvested, and her-1 protein purified.

EXAMPLE 10

Expression of her-1 Protein in an Insect Cell Expression System

In one aspect of the invention, the recombinant DNA molecules which produce her-1 protein in *S. frugiperda* cells comprise the cDNA of the 1.2 kb her-1 transcript inserted into a baculovirus transplacement vector. By transplacement vector is meant a plasmid in which the foreign gene of interest can be inserted downstream from the polyherin promoter. In addition, the transplacement vector contains sufficient amounts of the polyherin gene sequence to enable homologous recombination with the wild type baculovirus genome such that the progeny virus will now contain the her-1 cDNA sequence under the control of the viral polyherin promoter.

By utilizing the baculoviral promoter, the her-1 cDNA is expressed, and the her-1 protein processed and secreted from cells infected with the recombinant virus.

EXAMPLE 11

Introduction of her-1 into Soil and Ruminant Bacteria

In one embodiment of the invention, the rhizobacterium species is transformed with a vector carrying the cDNA of the 1.2 kb her-1 transcript. One particular preferred construction would employ the plasmid RSF1010 and derivatives thereof as described by Bagdasarian, M., Bagdasarian, M. M., Coleman, S., and Timmis, K. N. (1979) in *Plasmids of Medical, Environmental and Commercial Importance*, Timmis, K. N. and Puhler, A., eds., Elsevier/North Holland Biomedical Press, specifically incorporated herein by reference. The advantages of RSF1010 are that it is a relatively small, high copy number plasmid which is readily transformed into and stably maintained in both *E. coli* and Pseudomonas species. In this system, it would be preferred to use the Tac expression system as described for Escherichia, since it appears that the *E. coli* trp promoter is readily recognized by Pseudomonas RNA polymerase as set forth by Sakagucki (1982) Current Topics in Microbiology and Immunology 96:31–45, and Gray, G. L., McKeown, K. A., Jones, A. J. S., Seeburg, P. H., and Heyneker, H. L. in Biotechnology, Feb. 1984, pp., 161–165, both of which are specifically incorporated herein by reference. Transcriptional activity may be further maximized by requiring the exchange of the promoter with, e.g., an *E. coli* or *P. aeruginosa* trp promoter. Additionally, the lacI gene of *E. coli* would be included in the plasmid to effect regulation.

EXAMPLE 12

Expression of her-1 Protein in Plant Roots By Infection with Endophytic fungus

One preferred method of conferring nematode resistance to plants is to infect nematode-susceptible plants with genetically engineered endophytic fungi that accumulate in the plant root, for example, the endophyte *Glomus mosseae* which infects the roots of maize plants, as described in U.S. Pat. No. 4,550,527.

*G. mosseae* is cultured as described by Byrd et al. (1990) Curr. Genet. 18:347–354, specifically incorporated herein by reference. A vector carrying the cDNA of the 1.2 kb her-1 transcript will be constructed by methods known in the art such that the her-1 protein is expressed by the endophyte. Examples of fungal vectors known to the art include the pJP102 developed to transform filamentous fungi such as *Neurospora crassa* (Paietta and Marzluf (1985) in Molecular Genetics of Filamentous Fungi (Alan R. Liss, Inc., New York), pp. 1–13), the yeast vector YIp5 (Turner and Ballance (1985) in Gene Manipulations in Fungi (Academic Press, Inc., San Diego), pp. 259–278) and pDJB2 (Turner et al. (1985) in Molecular Genetics of Filamentous Fungi (Alan R. Liss, Inc., New York), pp. 15–28) for *Asperigillus nidulans*. Plants may be infected by a number of methods known in the art, including use of a root-penetrable carrier carrying an inoculum of the genetically engineered fungus, as described in U.S. Pat. No. 4,550,527. The fungi may also be transmitted maternally by infected seeds from laboratory plants infected with the engineered endophytes (White (1987) Plant Disease 71:340–342).

EXAMPLE 13

Plant Expression of her-1 Protein

In one embodiment of the invention, the cDNA of the 1.2 kb her-1 transcript is introduced into soybean seed tissue by particle acceleration, as described by McCabe et al. (1988) supra. The her-1 cDNA is ligated into the pCMC1022 plasmid, a pBR322-derived vector containing the cauliflower mosaic virus (CaMV) 35s promoter and the nopaline synthase polyadenylation region. The DNA coated projectiles are prepared by mixing 1.5–3 um gold spheres (Alfa Chemical Co.) with a solution of DNA, and drying the spheres on a plastic sheet, as described by McCabe et al. (1988) supra. The sheet is loaded onto a particle accelerating machine and impacted upon the target tissue, excised embryonic axes from immature soybean seed. The tissue is incubated to form multiple shoots capable of growing into viable transgenic plants expressing the her-1 protein.

In another embodiment of the invention, transgenic soybean plants capable of expressing the her-1 protein are produced using an Agrobacterium-mediated gene transfer system, as described by Hinchee et al. (1988) supra. The cDNA of the 1.2 kb her-1 transcript is ligated into the plant vector pMON9749 containing the CaMV 35s promoter, the NOS 3' polyadenylation signal, and the β-glucuronidase (GUS) gene as a histochemical marker for transformed cells. The vector is integrated into the disarmed Ti plasmid *A. tumefaciens* pTiT37-SE. Soybean cotyledon explants are inoculated with *A. tumefaciens* pTiT37-SE-pMON9749 and assayed for GUS activity, as described (Hinchee et al. (1988) supra). This method results in transgenic soybean plants which express the her-1 protein.

EXAMPLE 14

Direct Use of the her-1 Protein As a Means of Controlling Nematode Infestation of Plants and Animals her-1 produced in one of the cell expression systems described in Examples 8, 9, or 10, or a chemically synthesized mimetic with similar biological activity, is applied directly to plants and soil in an agronomically acceptable carrier, either in solution or powder form such that it contacts nematode embryos.

The her-1 protein produced in one the cell expression systems described above may be introduced into the drinking water or feed of nematode-infested animals such that the sexually-uncommitted nematode embryos and larvae are exposed to her-1 and induced to develope into males, thereby interrupting the cycle of nematode reproduction in the animals.

Humans and animals may also be treated with a pharmaceutical or veterinary composition comprising an effective amount of her-1 protein or mimetic or derivative thereof.

We claim:

1. A purified and isolated her-1 DNA encoding the amino acid sequence set forth in FIG. 3.

2. An expression vector for transforming a bacterium comprising expression regulatory sequences operatively linked to the DNA sequence of claim 1.

3. An *E. coli* host cell transformed with the expression vector of claim 2.

4. A purified and isolated DNA encoding her-1 consisting of the nucleic acid sequence which hybridizes to the complement of the nucleic acid sequence of claim 1 and encodes an amino acid sequence which induces male differentiation in nematodes.

5. A transformed bacterial host cell containing the expression vector of claim 2.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 623 base pairs
( B ) TYPE: nucleic acid
( C ) STRANDEDNESS: single
( D ) TOPOLOGY: linear ( i i ) MOLECULE TYPE: mRNA ( i i i ) HYPOTHETICAL: no ( i v ) ANTI-SENSE: no ( v i ) ORIGINAL SOURCE:
( A ) ORGANISM: Caenorhabditis elegans ( x i ) SEQUENCE DESCRIPTION: SEQ ID NO:1:

CTAGTTTCTT ATATATTAAG CAGAAACAAC GGACCAGTTC TTCAGCTTCT GAGAGTAGAT 60

TATATCTTAG GAGCATACAT GAGCACTGTA TGTACCTTCT TTGTCTAACT TTCTTTGAGT 120

```
ATCTAAGTCT CTTCAGGTTC TATATCCATC ATTCAACCAA ATGACACTGC AGGGATGCCT        180

ATCTCCTGAC TGAACCCACC AGTCGTCTCT TGCTCATATT CCTCCTACCT TCTGCTTCTA        240

TTTTCTCAGC GCATCTTGTC CACCTACAGT AGTAAATCTC CTCCCTTTCC TTACGTTGCA        300

TT  ATG AGA TAT CTC CCA ATT TTT GTG TTT CTC GGA TCA TTT GGC TAT ACG      350
    Met Arg Tyr Leu Pro Ile Phe Val Phe Leu Gly Ser Phe Gly Tyr Thr
    1               5                   10                  15

GAA ACT ACA TTA ACA AAG GAA CTT ATC AAA GAT GCA GCT GAG AAA TGC          398
Glu Thr Thr Leu Thr Lys Glu Leu Ile Lys Asp Ala Ala Glu Lys Cys
            20                  25                  30

TGT ACA AGA AAC CGT CAA GAA TGT TGC ATT GAA ATT ATG AAA TTT GGG          446
Cys Thr Arg Asn Arg Gln Glu Cys Cys Ile Glu Ile Met Lys Phe Gly
        35                  40                  45

TGAACCGCTT TTACGAGCAC GAACAATGCG ATAATCGGTA TAATTTAG A ACC CCA           501
                                                     Thr Pro
                                                     50

ATT CGA TGT GGT TAT GAC AGG GAT CCG AAG CTA CCC GGA TAT GTC TAC          549
Ile Arg Cys Gly Tyr Asp Arg Asp Pro Lys Leu Pro Gly Tyr Val Tyr
            55                  60                  65

AAA TGT CTT CAA AAT GTG TTG TTT GCA AAA GAA CCA AAG AAA AAG ATT          597
Lys Cys Leu Gln Asn Val Leu Phe Ala Lys Glu Pro Lys Lys Lys Ile
            70                  75                  80

AAC TTG GAT GGTGAGCGTT TTTTTT                                            623
Asn Leu Asp
        85
```

( 2 ) INFORMATION FOR SEQ ID NO:2:

( i ) SEQUENCE CHARACTERISTICS:
        ( A ) LENGTH: 1560 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: no ( i v ) ANTI-SENSE: no ( v i ) ORIGINAL SOURCE:
        ( A ) ORGANISM: Caenorhabditis elegans ( x i ) SEQUENCE DESCRIPTION: SEQ ID NO:2:

```
CCATTTGCCC ATCCCACGCC CTAATCTCAT ATTGTCTTTA TTCA GAC TCC GTG TGC         56
                                                 Asp Ser Val Cys

TGC TCC GTG TTT GGC AAC GAC CAA AAC GAT TCT GGA AGA AGA TGT GAG          104
Cys Ser Val Phe Gly Asn Asp Gln Asn Asp Ser Gly Arg Arg Cys Glu
90                  95                  100                 105

AAT CGT TGC AAG AAC CTC ATG ACC AGC CCT TCC ATC GAC GCT GCC ACA          152
Asn Arg Cys Lys Asn Leu Met Thr Ser Pro Ser Ile Asp Ala Ala Thr
            110                 115                 120

CGT CTG GAC AGC ATC AAA AGT TGC TCG CTT CTG GAT AAT GTA CTG TAT          200
Arg Leu Asp Ser Ile Lys Ser Cys Ser Leu Leu Asp Asn Val Leu Tyr
            125                 130                 135

AAA GTGAGTTTTT GTTAACACAG AATTTCAGTT CGCCTATTCT AGTTAGACAA               253
Lys

ACGGGTAAAT TGAAAATATT CGGTGCAATC TGTCTTATGG TTTTTTCAGC TCCTGCCTAT        313

TTCAGTACGT AGTCCTAATT TTTCCAGTTT TAAAGAAGG ATCCCTAGTT GACCAAAGCC         373

AAGTTTAAAA ATATTAAATT ATCTCCAACT CTGTAAAAAC GGCTGCGATT TGCAGACTTT        433
```

```
TTCTTGGTCC AGGCAAACAA TTTTGGAGTT CGTCCCATCC ATTCCCTCGT CTATAAAATT      493

CATCCTAAAA CGGAGAAAAT TAAAAAAAAA ATTCAATTGG CAAGCGGAAA ATCCGATAGT      553

GGATAGATAT CACCCCAAAA ATTGTTCGCC TAGGTTGAGA TACATTTTTG GAGCAGTGCG      613

TCAGTCCAGG AACCACGTTT TTCAAAGATA TCTCATTCGA TATTCTAATC GTTCAATTCG      673

AGTTAATCAA GTGTGTCATA AAACAAATTT ATTTTTCAG  TGT  TTT  GAG  AAA  TGC  CGG      730
                                            Cys  Phe  Glu  Lys  Cys  Arg
                                                                  140
```

```
AGC  CTC  CGT  AAA  GAT  GGT  ATC  AAA  ATT  GAA  GTG  CTC  CAA  TTC  GAA  GAA      778
Ser  Leu  Arg  Lys  Asp  Gly  Ile  Lys  Ile  Glu  Val  Leu  Gln  Phe  Glu  Glu
145                      150                 155                      160

TAC  TGC  AAT  GCA  ACG  TTT  ATC  CAA  AAG  CGA  ACT  TTC  CGA  GGA  GTC            823
Tyr  Cys  Asn  Ala  Thr  Phe  Ile  Gln  Lys  Arg  Thr  Phe  Arg  Gly  Val
                    165                      170                 175
```

```
TGAATCTGGG CTCATTAGCC TAAAACATCC CTAATCCGCC GTTGTCATTA TGGCACTCTC      883

CATCATGAGT GGTCCAATTT TTTCTTTTCT TTCTAAACCT TTTTATTTTA TTTTTTGTAA      943

CACCTCTATG TCTACCTCTT AATCAAAGCT TTGAGCTTTA CTCACTTTGA GTTATATTTT     1003

TAATCTTGTG TTCTCCTTAT GTTGAAGAAA ATTTTCGATA CGCAACTTGT CATATTGTTG     1063

TATATATTTT TAATAGAATT TTTTGAAATG TCCTATTCTT ATTGATTTCT TCTTAACATT     1123

CTCTTCAAGA ATGTTTTCGG ATGCGCTCAG ATGTCATGAA GGCGCACTAC GGTGCGTCCT     1183

GATTTATTT  ATTTTTTTT  TCATAAAAAA TATATCTTCT CTTGTTGGTT TCTCCTAAAG     1243

TTGTCAAATA GAATATTCAA GTACTTCTA  CGATCTTTTT TATTGAATAA ATTGTTTAT      1303

CAACGCACAG AACCCATCAA GTACTTCTA  CGATCTTTTT TATTGAATAA ATTGTTTAT      1363

CAACGCACAG AACCCATACG ACATAATCAA CAAAAAATGA TAAGAAAGTG ATTTTCGAAC     1423

TACAAATTTT ATCAATTTTT TTTCAATTCT CTGCTTTCTA ACAAATTCTA AATTTTATTT     1483

GTAATTTTAG TTATTCAACT GCAAAACGAG CAAAACTTTA TTTCTTATCG TTTTGAAAGA     1543

TTAATAACTA ATGTAAT                                                    1560
```

( 2 ) INFORMATION FOR SEQ ID NO:3:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( i i i ) HYPOTHETICAL: yes ( i x ) FEATURE:
        ( A ) NAME/KEY: her-1 protein
        ( B ) LOCATION: +1 to +175

( x i ) SEQUENCE DESCRIPTION: SEQ ID NO:3:

```
Met  Arg  Tyr  Leu  Pro  Ile  Phe  Val  Phe  Leu  Gly  Ser  Phe  Gly  Tyr  Thr
                    5                        10                      15

Glu  Thr  Thr  Leu  Thr  Lys  Glu  Leu  Ile  Lys  Asp  Ala  Ala  Glu  Lys  Cys
                    20                       25                      30

Cys  Thr  Arg  Asn  Arg  Gln  Glu  Cys  Cys  Ile  Glu  Ile  Met  Lys  Phe  Gly
          35                        40                       45

Thr  Pro  Ile  Arg  Cys  Gly  Tyr  Asp  Arg  Asp  Pro  Lys  Leu  Pro  Gly  Tyr
     50                       55                       60

Val  Tyr  Lys  Cys  Leu  Gln  Asn  Val  Leu  Phe  Ala  Lys  Glu  Pro  Lys  Lys
65                       70                       75                      80
```

```
Lys  Ile  Asn  Leu  Asp  Asp  Ser  Val  Cys  Cys  Ser  Val  Phe  Gly  Asn  Asp
               85                       90                       95

Gln  Asn  Asp  Ser  Gly  Arg  Arg  Cys  Glu  Asn  Arg  Cys  Lys  Asn  Leu  Met
              100                      105                      110

Thr  Ser  Pro  Ser  Ile  Asp  Ala  Ala  Thr  Arg  Leu  Asp  Ser  Ile  Lys  Ser
              115                      120                      125

Cys  Ser  Leu  Leu  Asp  Asn  Val  Leu  Tyr  Lys  Cys  Phe  Glu  Lys  Cys  Arg
     130                      135                      140

Ser  Leu  Arg  Lys  Asp  Gly  Ile  Lys  Ile  Glu  Val  Leu  Gln  Phe  Glu  Glu
145                      150                      155                      160

Tyr  Cys  Asn  Ala  Thr  Phe  Ile  Gln  Lys  Arg  Thr  Phe  Arg  Gly  Val
                    165                      170                      175
```

( 2 ) INFORMATION FOR SEQ ID NO:4:

( i ) SEQUENCE CHARACTERISTICS:
        ( A ) LENGTH: 64 amino acids
        ( B ) TYPE: amino acid
        ( D ) TOPOLOGY: linear ( i i ) MOLECULE TYPE: protein ( i i i ) HYPOTHETICAL: yes ( i x ) FEATURE:
        ( A ) NAME/KEY: her-1 protein
        ( B ) LOCATION: +1 to +64

( x i ) SEQUENCE DESCRIPTION: SEQ ID NO:4:

```
Met  Thr  Ser  Pro  Ser  Ile  Asp  Ala  Ala  Thr  Arg  Leu  Asp  Ser  Ile  Lys
                    5                       10                       15

Ser  Cys  Ser  Leu  Leu  Asp  Asn  Val  Leu  Tyr  Lys  Cys  Phe  Glu  Lys  Cys
               20                       25                       30

Arg  Ser  Leu  Arg  Lys  Asp  Gly  Ile  Lys  Ile  Glu  Val  Leu  Gln  Phe  Glu
               35                       40                       45

Glu  Tyr  Cys  Asn  Ala  Thr  Phe  Ile  Gln  Lys  Arg  Thr  Phe  Arg  Gly  Val
     50                       55                       60
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: DNA primer ( x i ) SEQUENCE DESCRIPTION: SEQ ID NO:5:

CACATCTTCT TCCAGAATCG         20

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: DNA primer ( x i ) SEQUENCE DESCRIPTION: SEQ ID NO:6:

GGCTCGAGGT CGACTCTAGA TT         22

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: DNA primer (xi) SEQUENCE DESCRIPTION: SEQ ID NO:7:

GTCGACTCTA GATTTTTTT TTTTTTT     27

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: DNA primer (xi) SEQUENCE DESCRIPTION: SEQ ID NO:8:

GAATCGTTTT GGTCGTTGCC     20